(12) United States Patent
Makino

(10) Patent No.: US 11,064,959 B2
(45) Date of Patent: Jul. 20, 2021

(54) ELECTRONIC CASSETTE, METHOD OF OPERATING ELECTRONIC CASSETTE, OPERATION PROGRAM FOR ELECTRONIC CASSETTE, CASSETTE CONTROL DEVICE, RADIOGRAPHY SYSTEM, AND METHOD OF OPERATING RADIOGRAPHY SYSTEM

(71) Applicant: FUJIFILM Corporation, Tokyo (JP)

(72) Inventor: Kazuhiro Makino, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 16/799,844

(22) Filed: Feb. 25, 2020

(65) Prior Publication Data
US 2020/0281548 A1  Sep. 10, 2020

(30) Foreign Application Priority Data

Mar. 7, 2019  (JP) ............................. JP2019-041888

(51) Int. Cl.
*A61B 6/00*  (2006.01)
(52) U.S. Cl.
CPC .............. *A61B 6/4283* (2013.01); *A61B 6/52* (2013.01); *A61B 6/4291* (2013.01)
(58) Field of Classification Search
CPC ........ A61B 6/4283; A61B 6/52; A61B 6/4291
See application file for complete search history.

(56) References Cited

U.S. PATENT DOCUMENTS

| 8,330,597 | B2 | 12/2012 | Nishino et al. | |
| 2009/0060136 | A1* | 3/2009 | Tamakoshi | H04N 5/232411 378/91 |
| 2009/0189761 | A1 | 7/2009 | Nishino et al. | |
| 2011/0254563 | A1* | 10/2011 | Liu | A61B 6/4208 324/538 |
| 2011/0317809 | A1* | 12/2011 | Eguchi | A61B 6/566 378/62 |
| 2014/0124678 | A1* | 5/2014 | Yoneyama | H04N 5/361 250/393 |
| 2015/0168566 | A1* | 6/2015 | Shikino | H04N 5/32 250/394 |
| 2015/0279196 | A1* | 10/2015 | Tajima | G08B 13/24 340/539.32 |
| 2015/0338531 | A1* | 11/2015 | Niekawa | H04N 5/3698 250/370.08 |

FOREIGN PATENT DOCUMENTS

JP  2009175104  8/2009

* cited by examiner

*Primary Examiner* — Blake C Riddick
(74) *Attorney, Agent, or Firm* — JCIPRNET

(57) ABSTRACT

The electronic cassette includes a portable housing. A CPU of the electronic cassette functions as a RW controller, a first determination unit, and a mode controller. The RW controller acquires a standard pose as a pose of the housing in a stored state, in which the housing is stored in a storage portion of a movable radiography apparatus, from a ROM. The first determination unit determines whether the housing is in the stored state or a taken-out state, in which the housing is taken out from the storage portion, based on the standard pose and a current pose as a current pose of the housing detected by a pose detection sensor. The mode controller switches the drive mode from the sleep mode to the radiography mode in a case where the first determination unit determines that the housing is brought from the stored state into the taken-out state.

19 Claims, 28 Drawing Sheets

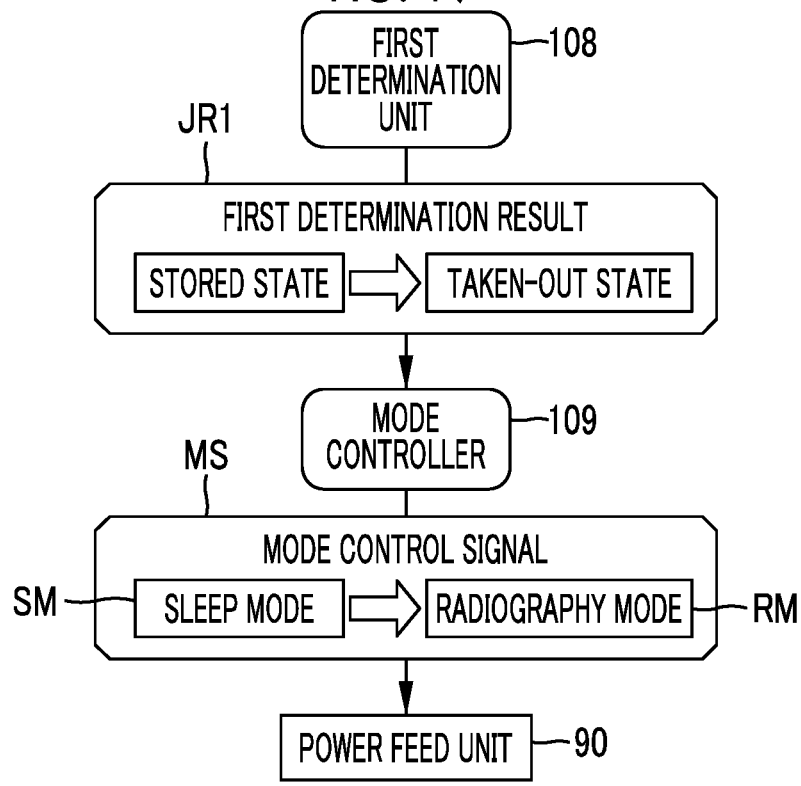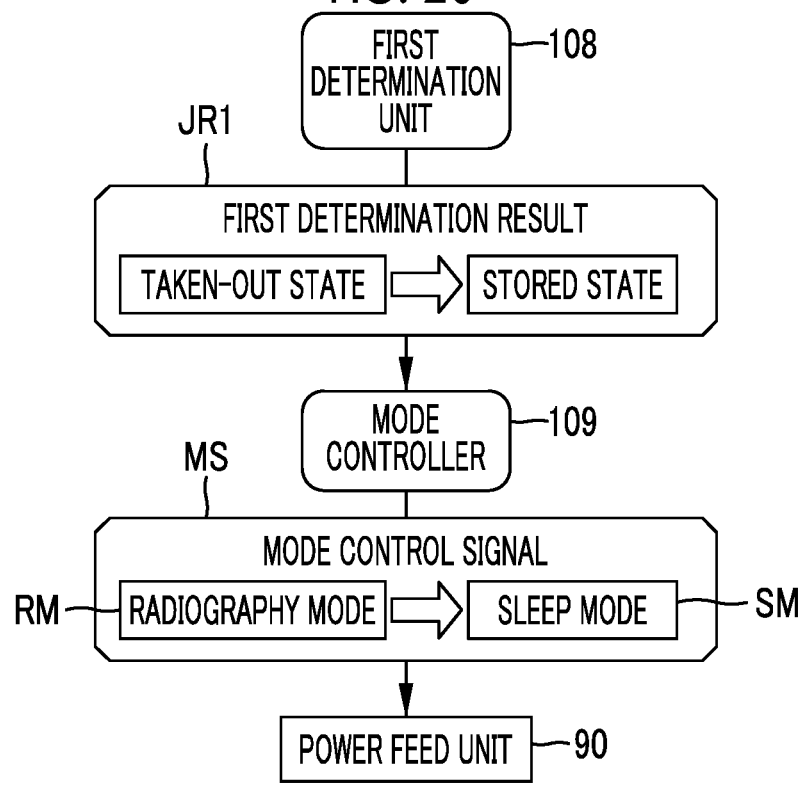

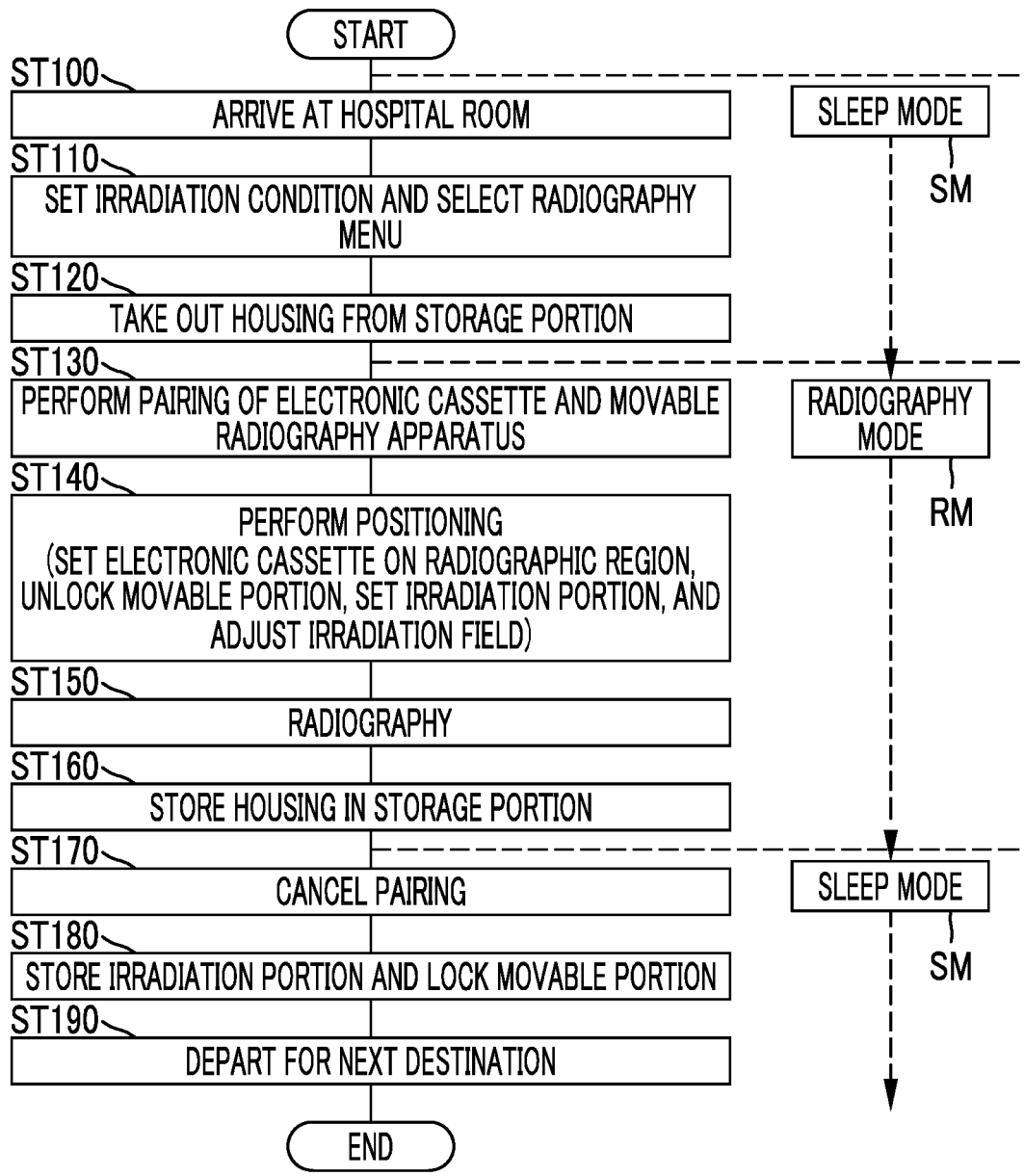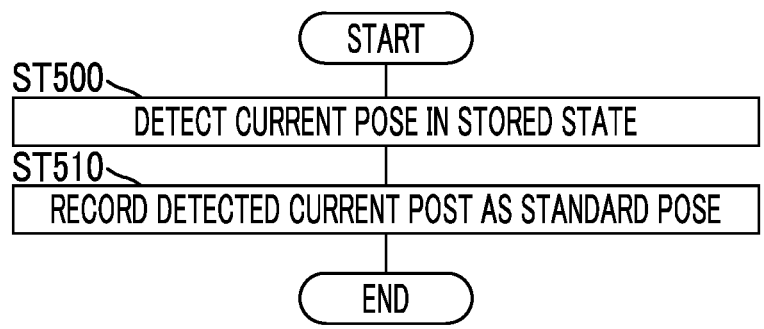

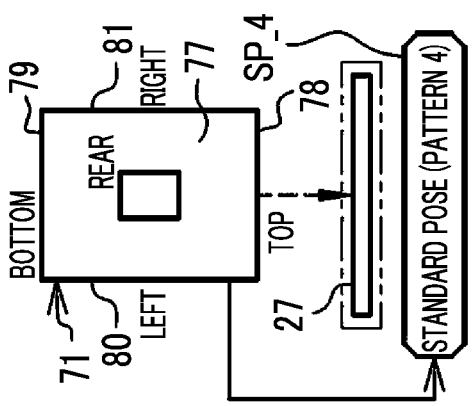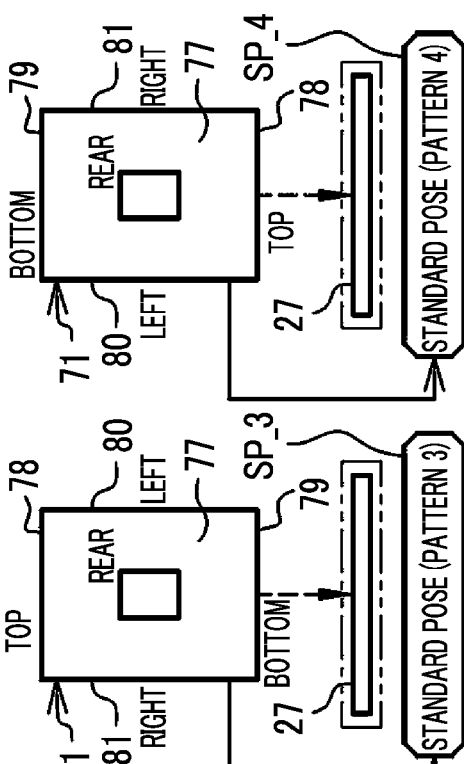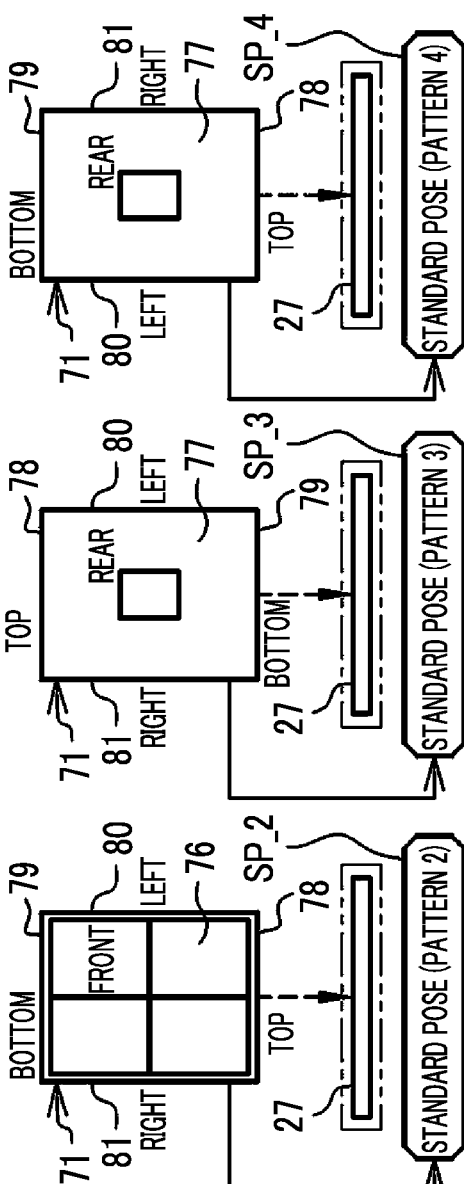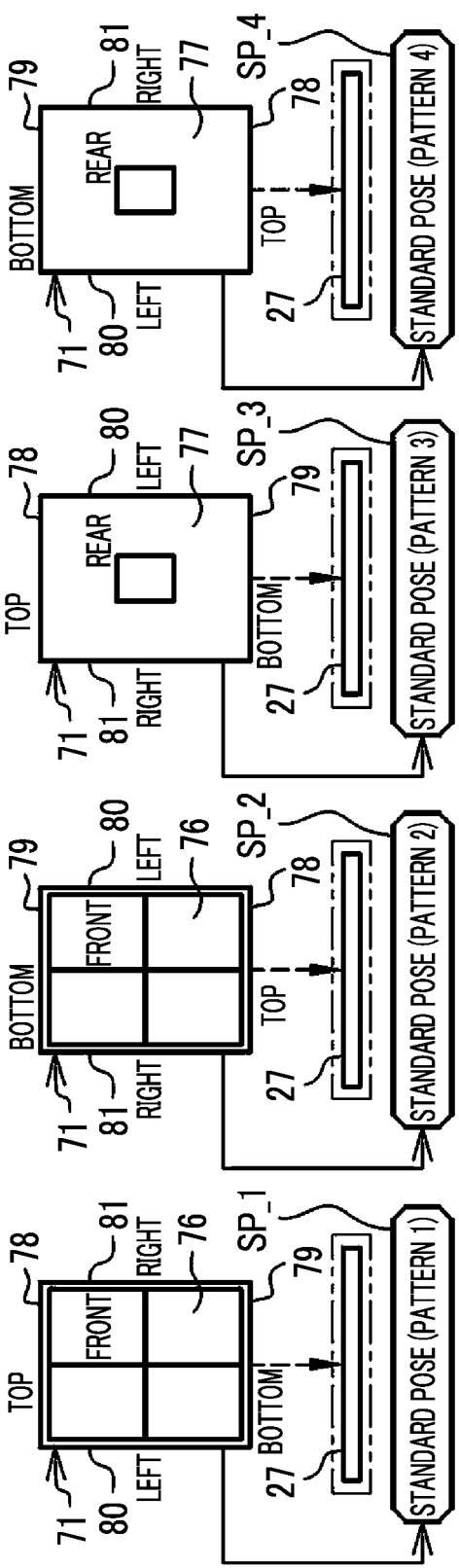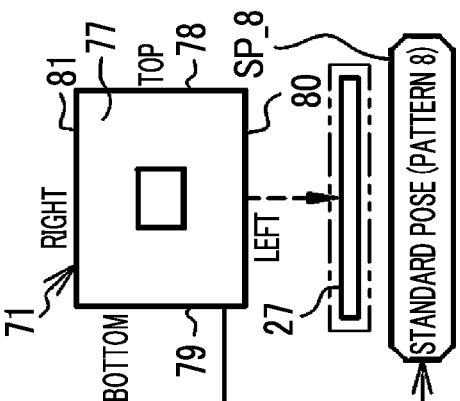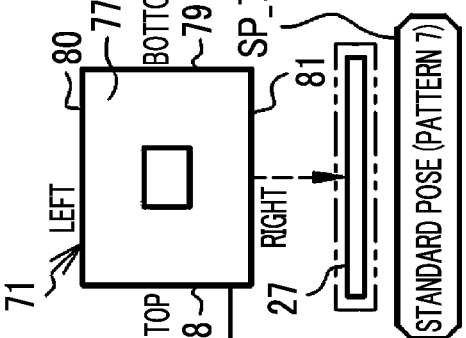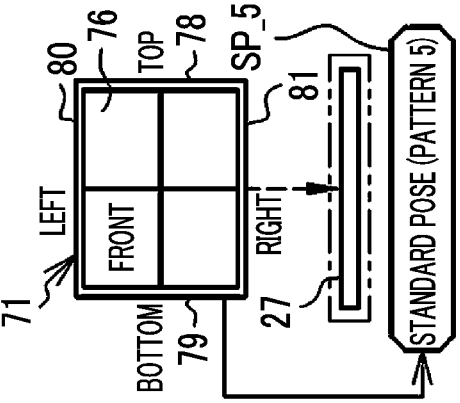

ELECTRONIC CASSETTE, METHOD OF OPERATING ELECTRONIC CASSETTE, OPERATION PROGRAM FOR ELECTRONIC CASSETTE, CASSETTE CONTROL DEVICE, RADIOGRAPHY SYSTEM, AND METHOD OF OPERATING RADIOGRAPHY SYSTEM

CROSS-REFERENCE TO RELATED APPLICATIONS

The present application claims priority under 35 U.S.C. § 119 to Japanese Patent Application No., 2019-041888 filed on Mar. 7, 2019. The above application is hereby expressly incorporated by reference, in its entirety, into the present application.

BACKGROUND

1. Technical Invention

A technique of the present disclosure relates to an electronic cassette, a method of operating an electronic cassette, an operation program for an electronic cassette, a cassette control device, a radiography system, and a method of operating a radiography system.

2. Description of the Related Art

In a medical site, a radiography using an electronic cassette is performed. As well known in the art, the electronic cassette comprises an image output unit that detects radiation transmitted through a subject and outputs a radiographic image represented by an electrical signal, and a portable housing in which the image output unit is incorporated. The housing is also incorporated with a battery and a wireless communication unit, and the electronic cassette can be used in a wireless manner.

On the other hand, in the medical site, patrol radiography in which an individual patient as a subject is subjected to radiography with a movable radiography apparatus mounted with the electronic cassette in hospital rooms is performed. The movable radiography apparatus is provided with a storage portion in which a housing of the electronic cassette is stored. The housing of the electronic cassette is stored in the storage portion, is moved along with the movable radiography apparatus, is taken out from the storage portion in a hospital room of a patient, and is used in radiography.

As the electronic cassette is driven with the battery as described above, wasteful power consumption should be minimized. For this reason, a majority of electronic cassettes have, as a drive mode, a sleep mode in which power consumption is smaller than a radiography mode in which a radiographic image can be output from an image output unit. The sleep mode is a drive mode in which power is selectively fed to a minimum needed portion, such as the wireless communication unit, on standby before radiography. Such an electronic cassette is brought into the sleep mode in a case where radiography is not used, and is brought into the radiography mode in a case where radiography is used.

JP2009-175104A describes an electronic cassette that switches a drive mode from a sleep mode to a radiography mode in a case where determination is made that a housing is lifted up by an operator, such as a radiographer. In more detail, the electronic cassette described in JP2009-175104A comprises a contact detection sensor that detects that the operator holds a grip provided in the housing, and a pose detection sensor (described as a direction detection sensor in JP2009-175104A) that detects that the housing is moved by the operator. Then, determination is made that the housing is lifted up by the operator from detection signals from the two sensors.

SUMMARY

In a case where the electronic cassette described in JP2009-175104A is mounted in a movable radiography apparatus to perform patrol radiography, for example, a case where mode control is performed such that the sleep mode is set in a case where the housing is stored in the storage portion and is moved along with the movable radiography apparatus, and the radiography mode is set in a case where the housing is taken out from the storage portion is considered. In this case, a method that determines a state of the housing from the detection signal of the contact detection sensor and performs the mode control is known. However, it is not possible to determine whether the detection signal of the pose detection sensor changes when the housing is taken out from the storage portion or when the housing is carried after taken out from the storage portion. Accordingly, in the electronic cassette described in JP2009-175104A, there is a concern that the mode control described above is not surely performed.

A technique of the present disclosure is to provide an electronic cassette, a method of operating an electronic cassette, an operation program for an electronic cassette, a cassette control device, a radiography system, and a method of operating a radiography system capable of surely performing control of a drive mode in patrol radiography using a movable radiography apparatus.

In order to achieve the above-described object, the present disclosure provides an electronic cassette comprising an image output unit that detects radiation transmitted through a subject and outputs a radiographic image represented by an electrical signal, a portable housing in which the image output unit is incorporated, a pose detection sensor that detects a current pose as a current pose of the housing, a first acquisition unit that acquires a standard pose as a pose of the housing in a stored state, in which the housing is stored in a storage portion of a movable radiography apparatus from a storage unit, a first determination unit that determines whether the housing is in the stored state or a taken-out state, in which the housing is taken out from the storage portion, based on the standard pose and the current pose, and a mode controller that controls a drive mode including a radiography mode where the radiographic image is able to be output from the image output unit and a sleep mode where power consumption is smaller than in the radiography mode, and switches the drive mode from the sleep mode to the radiography mode in a case where the first determination unit determines that the housing is brought from the stored state into the taken-out state.

It is preferable that the first determination unit determines that the housing is brought from the stored state into the taken-out state in a case where a state in which the current pose is deviated from the standard pose by a preset threshold value or more is continued for a preset period.

It is preferable that the mode controller switches the drive mode from the radiography mode to the sleep mode in a case where the first determination unit determines that the housing is brought from the taken-out state into the stored state.

It is preferable that the electronic cassette further comprises a second acquisition unit that acquires operation state information indicating an operation state of the movable radiography apparatus, and a second determination unit that determines whether or not the movable radiography apparatus is in a radiography preparation state based on the operation state information, and the mode controller does not perform switching from the sleep mode to the radiography mode in a case where the first determination unit determines that the housing is brought from the stored state into the taken-out state, and the second determination unit determines that the movable radiography apparatus is not in the radiography preparation state, and performs switching from the sleep mode to the radiography mode in a case where the first determination unit determines that the housing is brought from the stored state into the taken-out state, and the second determination unit determines that the movable radiography apparatus is in the radiography preparation state.

It is preferable that the movable radiography apparatus comprises an irradiation portion having a radiation tube that emits the radiation and being able to change a position with respect to the subject, and the operation state information is information indicating whether or not the irradiation portion is in a use state.

It is preferable that the mode controller does not perform switching from the sleep mode to the radiography mode in a case where the first determination unit determines that the housing is brought from the stored state into the taken-out state, and the operation state information has a content that the irradiation portion is not in the use state and the second determination unit determines that the movable radiography apparatus is not in the radiography preparation state, and performs switching from the sleep mode to the radiography mode in a case where the first determination unit determines that the housing is brought from the stored state into the taken-out state, the operation state information has a content that the irradiation portion is in the use state, and the second determination unit determines that the movable radiography apparatus is in the radiography preparation state.

It is preferable that the operation state information is information indicating whether or not a movable portion changing the position of the irradiation portion with respect to the subject is locked, and the second determination unit determines that the irradiation portion is not in the use state and the movable radiography apparatus is not in the radiography preparation state in a case where the movable portion is locked, and determines that the irradiation portion is in the use state and the movable radiography apparatus is in the radiography preparation state in a case where the movable portion is not locked.

It is preferable that the movable radiography apparatus comprises an irradiation field lamp that emits light representing an irradiation field of the radiation, and the operation state information is information indicating whether or not the irradiation field lamp is turned on.

It is preferable that the mode controller does not perform switching from the sleep mode to the radiography mode in a case where the first determination unit determines that the housing is brought from the stored state into the taken-out state, and the operation state information has a content that the irradiation field lamp is not turned on, and the second determination unit determines that the movable radiography apparatus is not in the radiography preparation state, and performs switching from the sleep mode to the radiography mode in a case where the first determination unit determines that the housing is brought from the stored state into the taken-out state, the operation state information has a content that the irradiation field lamp is turned on, and the second determination unit determines that the movable radiography apparatus is in the radiography preparation state.

It is preferable that the movable radiography apparatus comprises a communication unit, and the operation state information is information indicating whether or not communication with the communication unit is established.

It is preferable that the mode controller does not perform switching from the sleep mode to the radiography mode in a case where the first determination unit determines that the housing is brought from the stored state into the taken-out state, and the operation state information has a content that communication is not established, and the second determination unit determines that the movable radiography apparatus is not in the radiography preparation state, and performs switching from the sleep mode to the radiography mode in a case where the first determination unit determines that the housing is brought from the stored state into the taken-out state, the operation state information has a content that communication is established, and the second determination unit determines that the movable radiography apparatus is in the radiography preparation state.

It is preferable that the mode controller does not perform switching from the radiography mode to the sleep mode in a case where the first determination unit determines that the housing is brought from the taken-out state into the stored state, and the second determination unit determines that the movable radiography apparatus is in the radiography preparation state, and performs switching from the radiography mode to the sleep mode in a case where the first determination unit determines that the housing is brought from the taken-out state into the stored state, and the second determination unit determines that the movable radiography apparatus is not in the radiography preparation state.

It is preferable that a storage unit storing the standard pose is incorporated.

It is preferable that the housing is stored in the storage portion in a plurality of directions, a plurality of the standard poses are provided corresponding to the plurality of directions, and the first determination unit performs the determination based on the plurality of standard poses and the current pose.

The present disclosure also provides a method of operating an electronic cassette comprising an image output unit that detects radiation transmitted through a subject and outputs a radiographic image represented by an electrical signal, and a portable housing in which the image output unit is incorporated. The method comprises a first acquisition step of acquiring a standard pose as a pose of the housing in a stored state, in which the housing is stored in a storage portion of a movable radiography apparatus, from a storage unit, a first determination step of determining whether the housing is in the stored state or a taken-out state, in which the housing is taken out from the storage portion, based on the standard pose and a current pose as a current pose of the housing detected by a pose detection sensor, and a mode control step of controlling a drive mode including a radiography mode where the radiographic image is able to be output from the image output unit and a sleep mode where power consumption is smaller than in the radiography mode, and switching the drive mode from the sleep mode to the radiography mode in a case where determination is made in the first determination step that the housing is brought from the stored state into the taken-out state.

The present disclosure also provides an operation program for an electronic cassette comprising an image output unit that detects radiation transmitted through a subject and outputs a radiographic image represented by an electrical signal, and a portable housing in which the image output unit is incorporated. The operation program causes a computer to function as a first acquisition unit that acquires a standard pose as a pose of the housing in a stored state, in which the housing is stored in a storage portion of a movable radiography apparatus from a storage unit, a first determination unit that determines whether the housing is in the stored state or a taken-out state, in which the housing is taken out from the storage portion, based on the standard pose and a current pose as a current pose of the housing detected by a pose detection sensor, and a mode controller that controls a drive mode including a radiography mode where the radiographic image is able to be output from the image output unit and a sleep mode where power consumption is smaller than in the radiography mode, and switches the drive mode from the sleep mode to the radiography mode in a case where the first determination unit determines that the housing is brought from the stored state into the taken-out state.

The present disclosure also provides a cassette control device for controlling an electronic cassette comprising an image output unit that detects radiation transmitted through a subject and outputs a radiographic image represented by an electrical signal and a portable housing in which the image output unit is incorporated. The cassette control device comprises a first acquisition unit that acquires a standard pose as a pose of the housing in a stored state, in which the housing is stored in a storage portion of a movable radiography apparatus from a storage unit, a first determination unit that determines whether the housing is in the stored state or a taken-out state, in which the housing is taken out from the storage portion, based on the standard pose and a current pose as a current pose of the housing detected by a pose detection sensor, and a mode controller that controls a drive mode of the electronic cassette including a radiography mode where the radiographic image is able to be output from the image output unit and a sleep mode where power consumption is smaller than in the radiography mode, and switches the drive mode from the sleep mode to the radiography mode in a case where the first determination unit determines that the housing is brought from the stored state into the taken-out state.

The present disclosure also provides a radiography system comprising an electronic cassette having an image output unit that detects radiation transmitted through a subject and outputs a radiographic image represented by an electrical signal and a portable housing in which the image output unit is incorporated, a movable radiography apparatus having a storage portion, in which the electronic cassette is stored, a first acquisition unit that acquires a standard pose as a pose of the housing in a stored state, in which the housing is stored in the storage portion, from a storage unit, a first determination unit that determines whether the housing is in the stored state or a taken-out state, in which the housing is taken out from the storage portion, based on the standard pose and a current pose as a current pose of the housing detected by a pose detection sensor, and a mode controller that controls a drive mode of the electronic cassette including a radiography mode where the radiographic image is able to be output from the image output unit and a sleep mode where power consumption is smaller than in the radiography mode, and switches the drive mode from the sleep mode to the radiography mode in a case where the first determination unit determines that the housing is brought from the stored state into the taken-out state.

The present disclosure also provides a method of operating a radiography system comprising an electronic cassette having an image output unit that detects radiation transmitted through a subject and outputs a radiographic image represented by an electrical signal and a portable housing in which the image output unit is incorporated, and a movable radiography apparatus having a storage portion, in which the electronic cassette is stored. The method comprises a first acquisition step of acquiring a standard pose as a pose of the housing in a stored state, in which the housing is stored in the storage portion, from a storage unit, a first determination step of determining whether the housing is in the stored state or a taken-out state, in which the housing is taken out from the storage portion, based on the standard pose and a current pose as a current pose of the housing detected by a pose detection sensor, and a mode control step of controlling a drive mode of the electronic cassette including a radiography mode where the radiographic image is able to be output from the image output unit and a sleep mode where power consumption is smaller than in the radiography mode, and switching the drive mode from the sleep mode to the radiography mode in a case where determination is made in the first determination step that the housing is brought from the stored state into the taken-out state.

According to the technique of the present disclosure, it is possible to provide an electronic cassette, a method of operating an electronic cassette, an operation program for an electronic cassette, a cassette control device, a radiography system, and a method of operating a radiography system capable of surely performing control of a drive mode in a patrol radiography using a movable radiography apparatus.

BRIEF DESCRIPTION OF THE DRAWINGS

Exemplary embodiments according to the technique of the present disclosure will be described in detail based on the following figures, wherein:

FIG. 19 is a diagram showing a manner of mode control in a case where the first determination condition is the content shown in FIG. 15;

FIG. 20 is a diagram showing a manner of mode control in a case where the first determination condition is the content shown in FIG. 18;

FIG. 21 is a flowchart showing a procedure of radiography with a radiography system in a certain hospital room;

FIG. 22 is a flowchart showing a processing procedure of the electronic cassette;

FIGS. 43A to 43H are diagrams showing a pattern of a storage direction in the storage portion of the housing, and specifically, FIG. 43A shows a pattern 1, FIG. 43B shows a pattern 2, FIG. 43C shows a pattern 3, FIG. 43D shows a pattern 4, FIG. 43E shows a pattern 5, FIG. 43F shows a pattern 6, FIG. 43G shows a pattern 7, and FIG. 43H shows a pattern 8;

DETAILED DESCRIPTION

First Embodiment

Figure 1:
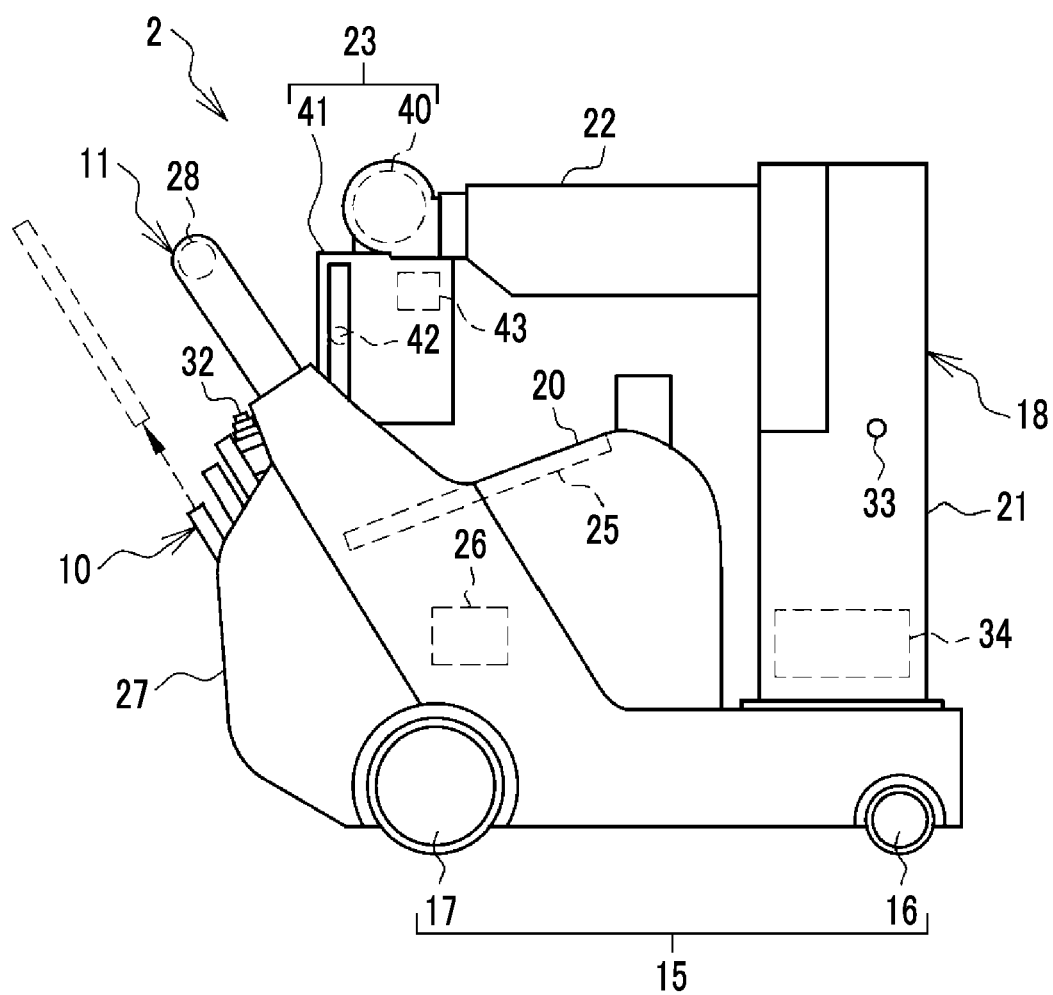
FIG. 1 is a diagram showing a radiography system.

In FIG. 1, a radiography system 2 comprises an electronic cassette 10 and a movable radiography apparatus 11. The radiography system 2 is a system that subjects an individual patient P (see FIG. 2) as a subject to radiography with the movable radiography apparatus 11 mounted with the electronic cassette 10 in hospital rooms.

The movable radiography apparatus 11 comprises a carriage 15. The carriage 15 has four wheels including a pair of right and left front wheels 16 and a pair of right and left rear wheels 17. The front wheels 16 are turnable right and left. The rear wheels 17 are of a so-called electric assistant type in which the right and left wheels are rotationally driven independently by motors or the like. For example, in a case where a rotation speed of the right rear wheel 17 is made higher than that of the left rear wheel 17, the movable radiography apparatus 11 turns to the left. On the other hand, in a case where the rotation speed of the left rear wheel 17 is made higher than that of the right rear wheel 17, the movable radiography apparatus 11 turns to the right. The movable radiography apparatus 11 is movable in a hospital with the carriage 15.

A body portion 18 is provided on the carriage 15. The body portion 18 has a center portion 20, a column portion 21, an arm portion 22, an irradiation portion 23, and the like. The movable radiography apparatus 11 is moved in a state shown in FIG. 1 in which the column portion 21 and the arm portion 22 are retracted, and the irradiation portion 23 is stored in an upper portion of the center portion 20.

The center portion 20 has a console 25, a communication unit 26, a storage portion 27, and a handle 28. The console 25 is embedded in an inclined upper surface of the center portion 20. The console 25 is constituted of a console table 30 and a display 31 (see FIG. 4 together). The console table 30 is operated by an operator OP (see FIG. 2), such as a radiographer, in setting an irradiation condition of radiation, in selecting a radiography menu, or the like. The display 31 displays various screens, a setting screen of the irradiation condition and a selection screen of the radiography menu, a radiographic image, and the like. The radiography menu is represented by a set of a radiography region, a radiography direction, and a radiography pose, such as front chest decubitus.

The communication unit 26 performs wireless communication or wired communication with the electronic cassette 10. The communication unit 26 transmits the irradiation condition to the electronic cassette 10. The communication unit 26 receives a radiographic image from the electronic cassette 10.

Figure 5:
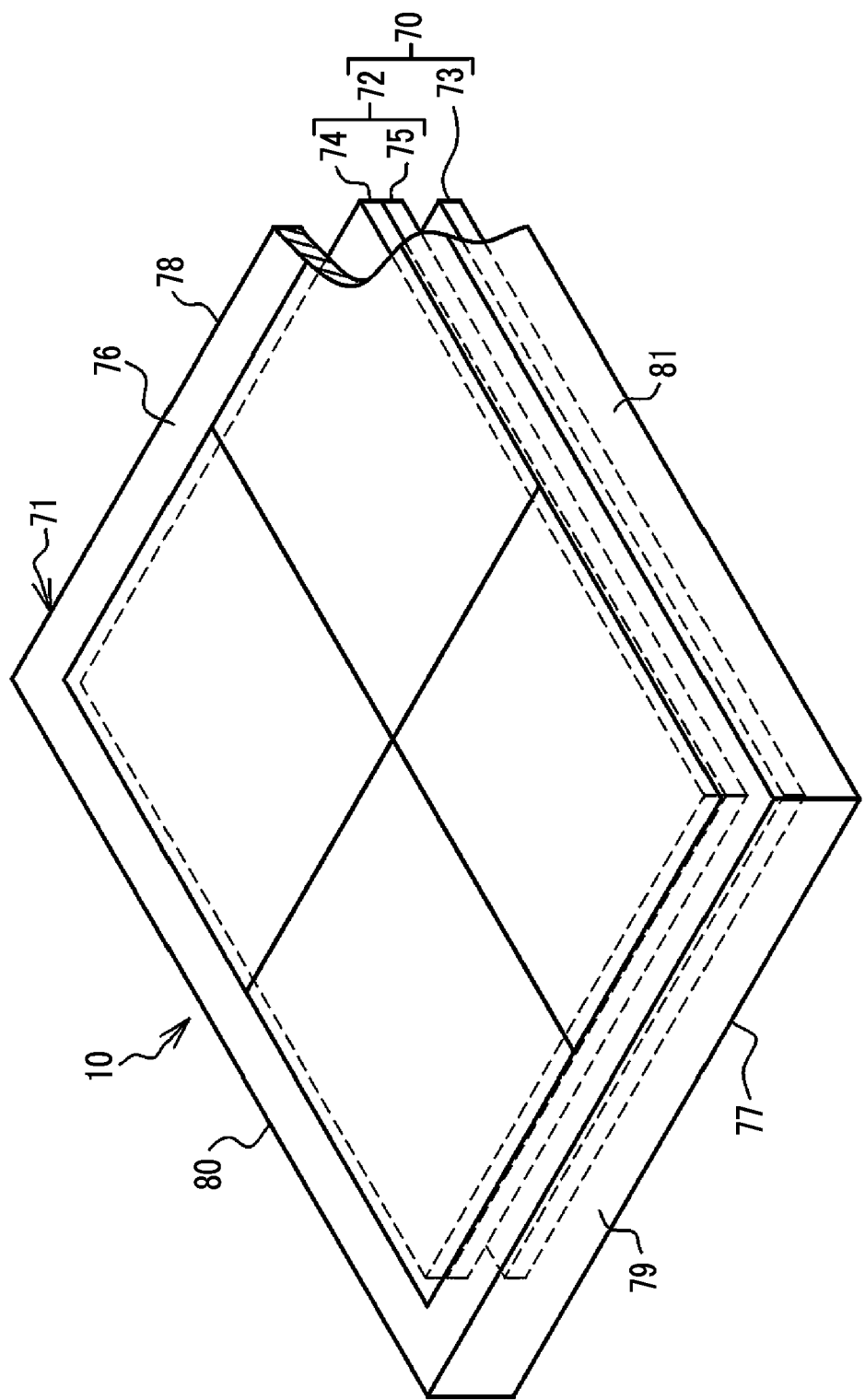
FIG. 5 is an appearance perspective view of an electronic cassette as viewed from a front surface.
Figure 6:
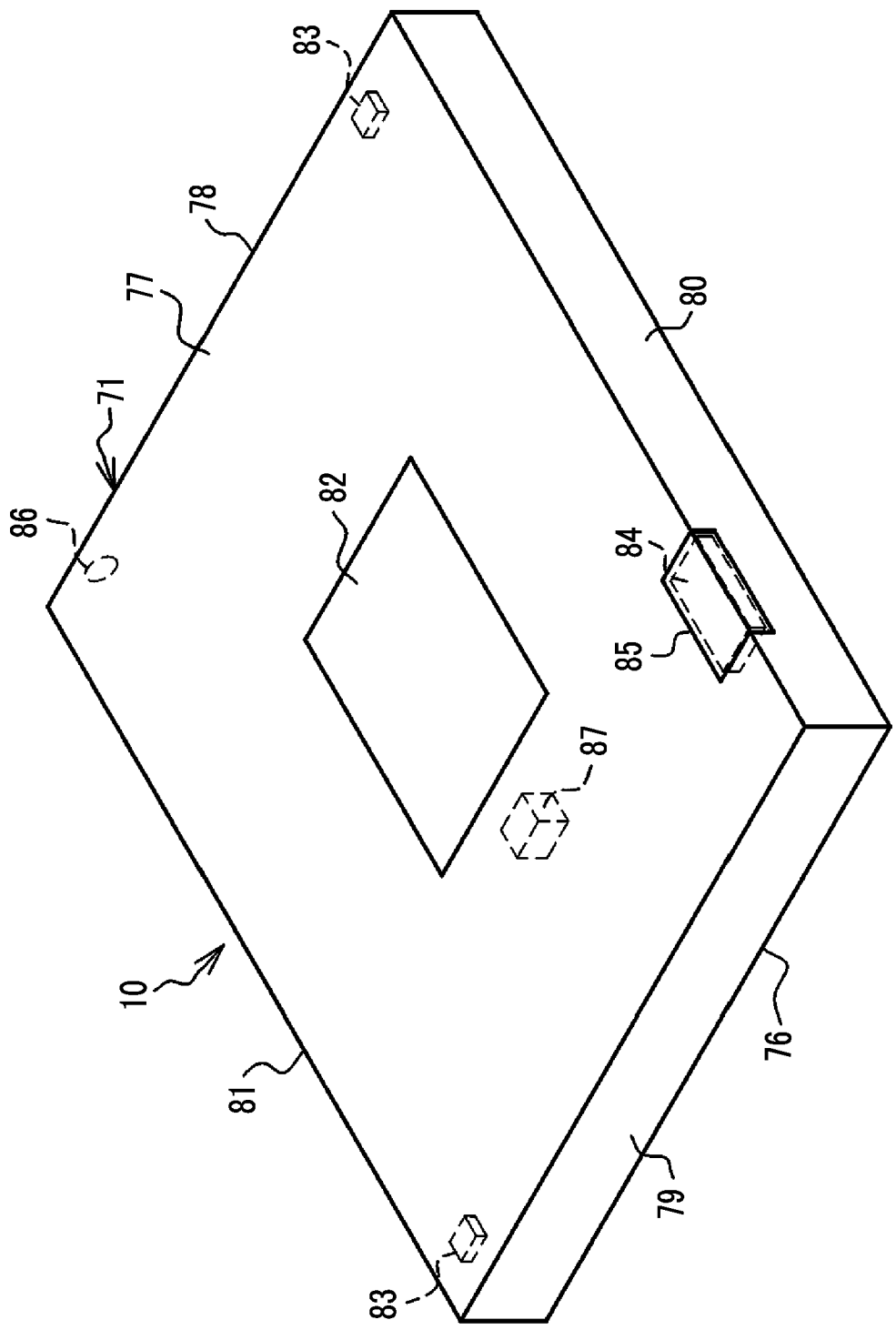
FIG. 6 is an appearance perspective view of the electronic cassette as viewed from a rear surface.

The storage portion 27 is disposed in a rear surface of the center portion 20. The storage portion 27 stores a housing 71 (see FIGS. 5 and 6) of the electronic cassette 10. In regard to the electronic cassette 10, there are a plurality of kinds of housings 71 of longitudinal/lateral sizes of 17 inches×17 inches, 17 inches×14 inches, 12 inches×10 inches, and the like. The storage portion 27 can store a plurality of kinds of housings 71 of the electronic cassettes 10 regardless of the kinds. The storage portion 27 is inclined, and the housing 71 is stored in an inclined state. Hereinafter, a state in which the housing 71 is stored in the storage portion 27 is referred to as a stored state (see FIG. 10). On the other hand, a state in which the housing 71 is taken out from the storage portion 27 is referred to as a taken-out state (see FIG. 10). The storage portion 27 is provided with a function of charging a battery 82 (see FIG. 6) of the electronic cassette 10.

The handle 28 is provided at a position protruding upward of the center portion 20. The handle 28 has a circular columnar shape that is long in a right-left direction. The handle 28 is held by the operator OP in order to control the carriage 15 (see FIG. 4).

An irradiation switch 32 is attached to an upper portion of the storage portion 27. The irradiation switch 32 is a switch that is provided to allow the operator OP to give an instruction to start irradiation of radiation. An extension cable (not shown) is connected to the irradiation switch 32, and can be removed from the center portion 20 for use. The irradiation switch 32 is, for example, a two-stage push switch. The irradiation switch 32 generates a warm-up instruction signal when being pushed to the first stage (half-pushed), and generates an irradiation start instruction signal when being pushed to the second stage (fully pushed). Though not shown, the center portion 20 is incorporated with a battery that supplies electric power to each unit.

The column portion 21 has a prismatic columnar shape, and is disposed at a position above the front wheels 16 and at a center position of the carriage 15 in the right-left direction. The column portion 21 is provided with a lock and unlock switch 33. In the column portion 21, a voltage generator 34 is provided.

The arm portion 22 has the same prismatic columnar shape as the column portion 21. The arm portion 22 has a base end that is attached to the column portion 21, and a distal end that becomes a free end on an opposite side of the base end and to which the irradiation portion 23 is attached.

The irradiation portion 23 is constituted of a radiation tube 40 and an irradiation field limiter 41. The radiation tube 40 emits, for example, X-rays as radiation. The radiation tube 40 is provided with a filament, a target, a grid electrode, and the like (all are not shown). A voltage from the voltage generator 34 is applied between the filament as a cathode and the target as an anode. The voltage that is applied between the filament and the target is referred to as a tube voltage. The filament discharges thermoelectrons according to the applied tube voltage toward the target. The target radiates radiation with collision of the thermoelectrons from the filament. The grid electrode is disposed between the filament and the target. The grid electrode changes a flow rate of the thermoelectrons from the filament toward the target according to the voltage applied from the voltage generator 34. The flow rate of the thermoelectrons from the filament toward the target is referred to as a tube current. The tube voltage and the tube current are set as irradiation conditions along with an irradiation time.

In a case where the irradiation switch 32 is half-pushed and the warm-up instruction signal is generated, the filament is warmed up and the rotation of the target is started. When the filament reaches a prescribed temperature, and the target reaches a prescribed rotation speed, warm-up is completed. In a case where the irradiation switch 32 is fully pushed and the irradiation start instruction signal is generated in a state in which the warm-up is completed, the tube voltage is applied from the voltage generator 34, and radiation is generated from the radiation tube 40. When the irradiation time set in the irradiation conditions has elapsed from the start of generation of radiation, the application of the tube voltage is stopped, and irradiation of radiation ends.

The irradiation field limiter 41 limits an irradiation field of radiation generated from the radiation tube 40. For example, the irradiation field limiter 41 has a configuration in which four shield plates formed of lead or the like shielding radiation are disposed on the respective sides of a quadrangle, and an emission opening of the quadrangle transmitting radiation is formed in a center portion. The irradiation field limiter 41 changes the positions of the shield plates to change the size of the emission opening, and accordingly, changes the irradiation field of radiation.

The irradiation field limiter 41 is also provided with the same lock and unlock switch 42 as in the column portion 21. In the irradiation field limiter 41, an irradiation field lamp 43 that emits light (for example, white light) representing the irradiation field is provided.

Figure 2:
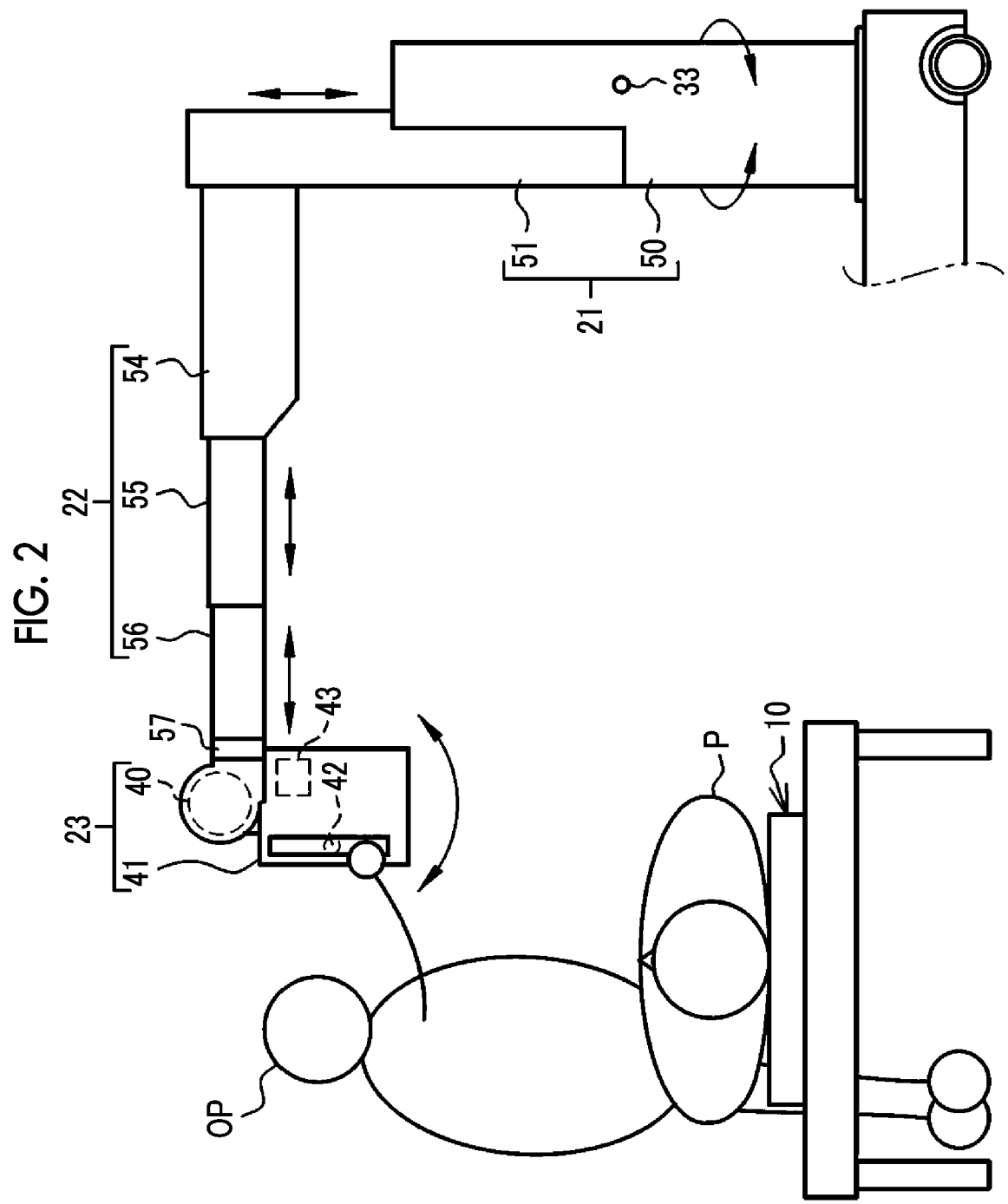
FIG. 2 is a diagram showing a rotation direction and a movement direction of a column portion, a movement direction of an arm portion, and a rotation direction of an irradiation portion.

As shown in FIG. 2, the column portion 21 has a first column 50 and a second column 51. The first column 50 is provided on an upper surface of the carriage 15. The first column 50 can rotate with respect to the carriage 15. The second column 51 can move in an up-down direction with respect to the first column 50. The rotation of the first column 50 and the up-down movement of the second column 51 can be unlocked by operating the lock and unlock switch 33.

The arm portion 22 has a fixed arm 54, a first arm 55, and a second arm 56. The fixed arm 54 is bent at right angles with respect to the second column 51. A base end of the fixed arm 54 is attached to the second column 51. The first arm 55 is attached to a distal end of the fixed arm 54. That is, the fixed arm 54 connects the second column 51 and the first arm 55. The irradiation portion 23 is attached to a distal end of the second arm 56 through a swing portion 57. The first arm 55 can move in a front-rear direction with respect to the fixed arm 54. The second arm 56 can move in a front-rear direction with respect to the first arm 55. The front-rear movement of the first arm 55 and the front-rear movement of the second arm 56 can be unlocked by operating the lock and unlock switch 42.

Figure 3:
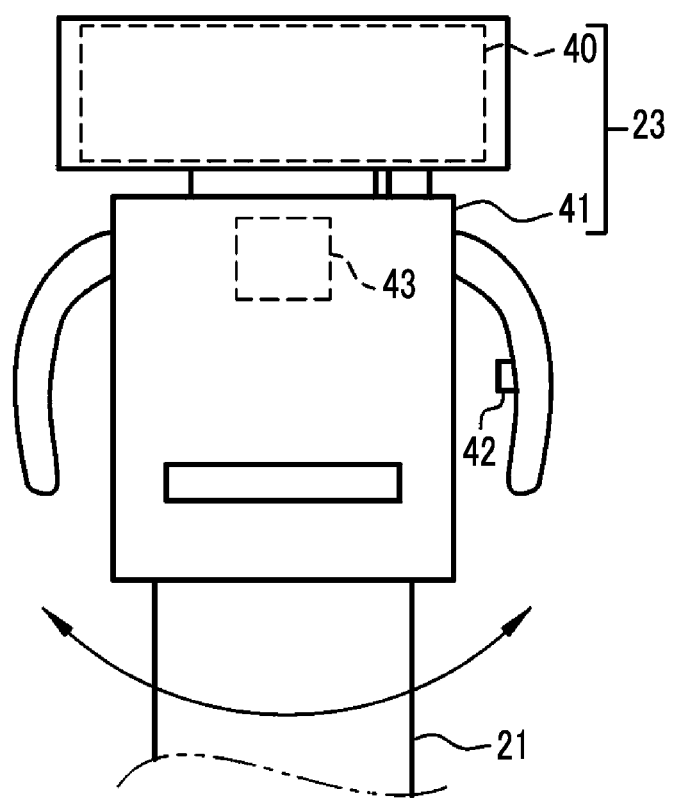
FIG. 3 is a diagram showing the rotation direction of the irradiation portion.

The irradiation portion 23 can be rotated around an axis parallel with a width direction thereof by the swing portion 57. As shown in FIG. 3, the irradiation portion 23 can also be rotated around an axis parallel with a front-rear direction thereof. The rotation of the irradiation portion 23 around the two axes by the swing portion 57 can be unlocked by operating the lock and unlock switch 42 like the front-rear movement of the first arm 55 and the front-rear movement of the second arm 56.

The position of the irradiation portion 23 with respect to the patient P is changed by the rotation of the first column 50 and the up-down movement of the second column 51. Furthermore, the position of the irradiation portion 23 with respect to the patient P is changed by the front-rear movement of the first arm 55 and the front-rear movement of the second arm 56. In addition, the position of the irradiation portion 23 with respect to the patient P is changed by the rotation of the irradiation portion 23 around the two axes by the swing portion 57. That is, the column portion 21, the arm portion 22, and the swing portion 57 are an example of a "movable portion" related to the technique of the present disclosure.

Figure 4:
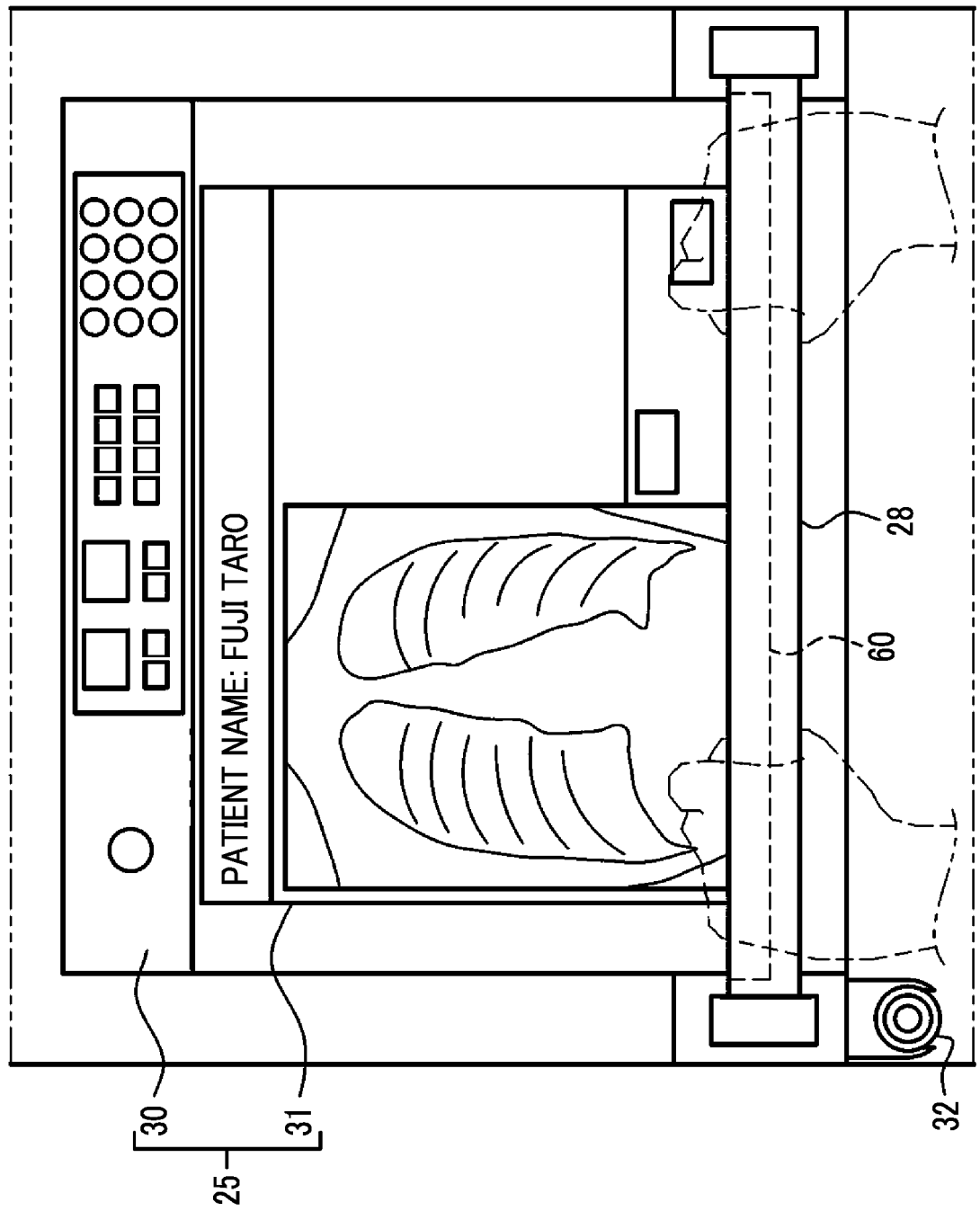
FIG. 4 is a diagram showing a body portion as viewed from an upper surface.

As shown in FIG. 4, around a front portion of the handle 28, an unlock switch 60 that unlocks the rotation of the rear wheels 17 is provided. The unlock switch 60 detects that the operator OP holds the handle 28. The unlock switch 60 is, for example, a sensor that detects contact of a hand with change in static capacitance or a sensor that detects contact of the hand with change in temperature. Alternatively, the unlock switch 60 may be a mechanical lever switch that protrudes from a surface of the handle 28 and is turned off when the handle 28 is not held with the hands, and is retracted in the handle 28 and is turned on when the handle 28 is held with the hands. In FIG. 4, a state in which the operator OP holds the handle 28 with both hands is shown by a dotted line. [0049] In FIGS. 5 and 6, the electronic cassette 10 comprises an image output unit 70 that detects radiation transmitted through the patient P and outputs a radiographic image represented by an electrical signal, and a portable housing 71 in which the image output unit 70 is incorporated. The image output unit 70 has a radiation detection unit 72 and a circuit unit 73. The radiation detection unit 72 is constituted of a scintillator 74 and a light detection substrate 75.

The scintillator 74 and the light detection substrate 75 are laminated in an order of the scintillator 74 and the light detection substrate 75 as viewed from a front surface 76 of the housing 71 on which radiation is incident. The scintillator 74 has a phosphor, such as thallium-activated cesium iodide (CsI:Tl) or terbium-activated gadolinium oxysulfide (GOS, $Gd_2O_2S$:Tb), and converts incident radiation to visible light and discharges visible light. The light detection substrate 75 detects visible light discharged from the scintillator 74 and converts visible light to an electrical signal. In more detail, the light detection substrate 75 has a plurality of pixels arranged in a two-dimensional matrix. As well known in the art, each pixel has a photoelectric conversion unit that generates electric charge (electron-hole pair) with incidence of visible light and accumulates the electric charge, and a switching element that controls accumulation of the electric charge in the photoelectric conversion unit and reading of the electric charge from the photoelectric conversion unit, such as a thin film transistor (TFT). The circuit unit 73 controls the drive of the switching element or the like of the light detection substrate 75, and generates a radiographic image based on the electrical signal output from the light detection substrate 75. The scintillator 74 and the light detection substrate 75 may be laminated in an order of the light detection substrate 75 and the scintillator 74 as viewed from the front surface 76. The electronic cassette 10 may be a direct conversion type electronic cassette that directly converts radiation to an electrical signal, not an indirect conversion type electronic cassette that converts radiation converted to visible light with the scintillator 74 of the example to an electrical signal.

The housing 71 has a rectangular parallelepiped shape having the front surface 76, a rear surface 77 facing the front surface 76, and four side surfaces 78, 79, 80, and 81 on upper, lower, right, and left sides. The battery 82 is attachably and detachably loaded in a center portion of the rear surface 77. The battery 82 is a rechargeable secondary battery. In corner portions facing the upper surface 78 and the lower surface 79, a pair of antennas 83 for wireless communication is incorporated. In the left surface 80, a connector 84 to which a cable for wired communication from the movable radiography apparatus 11 is connected is provided. The connector 84 is covered with a cover 85 at the time of non-use. In a case where wireless communication is performed by the antennas 83, the electronic cassette 10 is driven with electric power from the battery 82 and can be used in a wireless manner.

Figure 7:
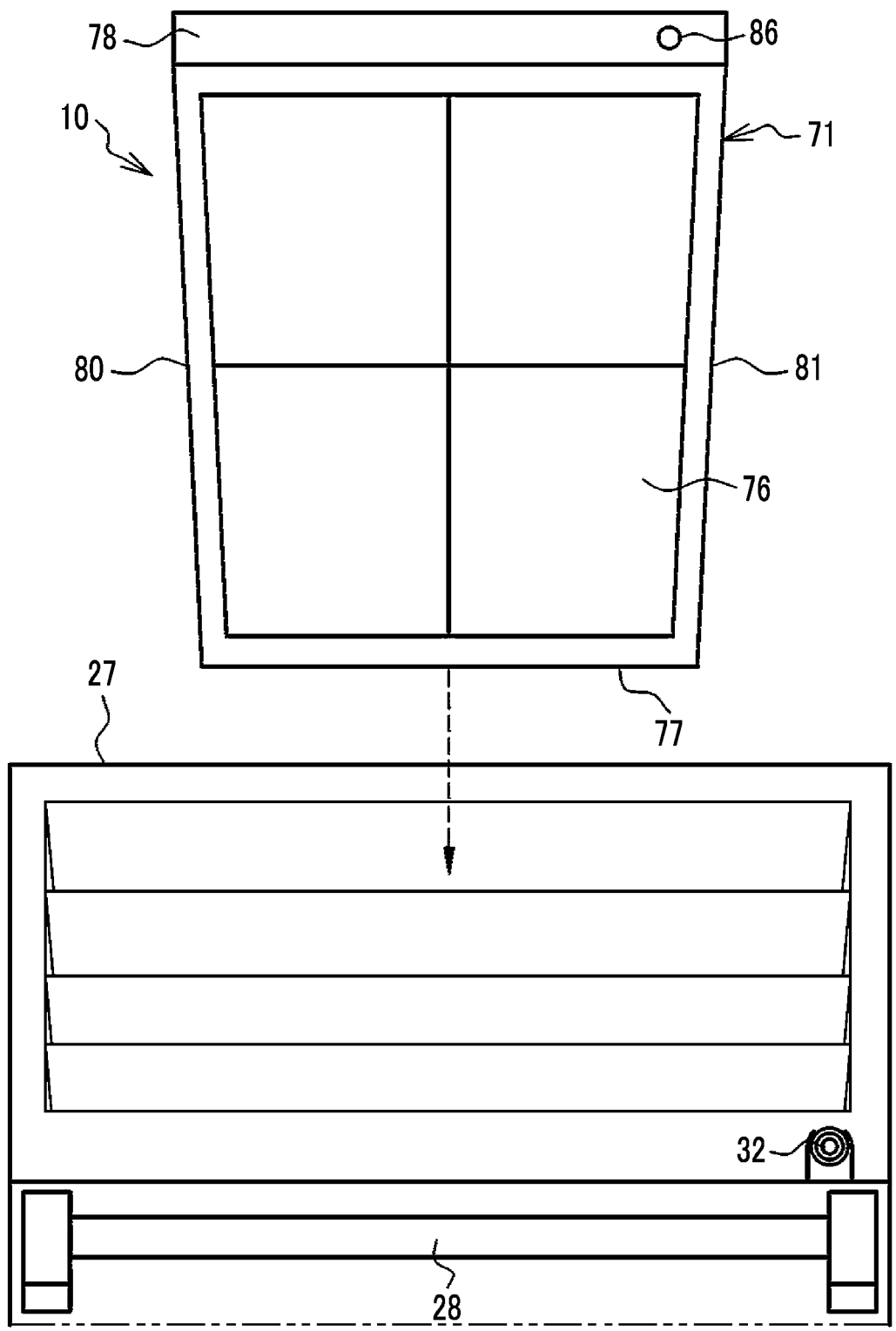
FIG. 7 is a diagram showing a direction of the electronic cassette that is stored in a storage portion.

In the upper surface 78, a standard pose recording button 86 that records a standard pose SP (see FIG. 9) as a pose of the housing 71 in the stored state is provided (also see FIG. 7). In the housing 71, a pose detection sensor 87 is incorporated. The pose detection sensor 87 detects a current pose CP (see FIG. 9) as a current pose of the housing 71. The pose detection sensor 87 is, for example, a three-axis acceleration sensor, a three-axis angular velocity sensor, a three-axis terrestrial magnetism sensor, or the like. In addition, the housing 71 is provided with a main power supply switch that turns on and off a main power supply, an indicator (not shown) that notifies of a drive mode DM (see FIG. 10) of the electronic cassette 10, such as a radiography mode RM and a sleep mode SM, and the like.

As shown in FIG. 7, the housing 71 is stored in the storage portion 27 from the lower surface 79 such that the front surface 76 turns toward the handle 28. In directions other than the direction shown in FIG. 7, it is not possible to store the housing 71 in the storage portion 27. That is, in the embodiment, the housing 71 is stored in the storage portion 27 in one direction.

Figure 8:
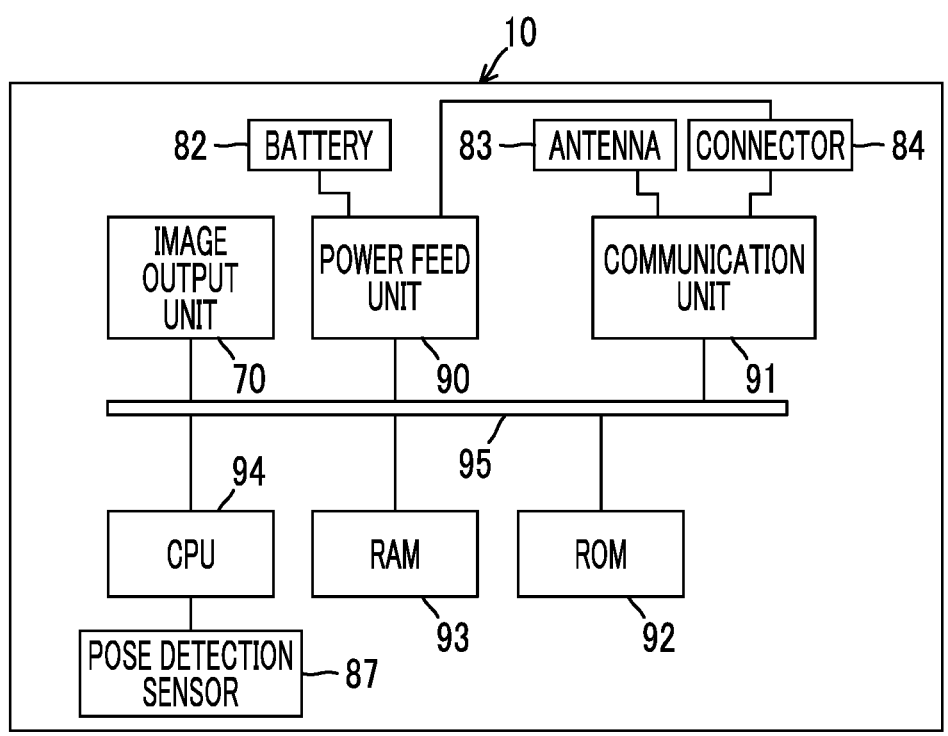
FIG. 8 is a block diagram of the electronic cassette.

In FIG. 8, the electronic cassette 10 comprises a power feed unit 90, a communication unit 91, a read only memory (ROM) 92, a random access memory (RAM) 93, and a central processing unit (CPU) 94, in addition to the above-described image output unit 70. The units are connected to one another through a busline 95. The ROM 92, the RAM 93, the CPU 94, and the busline 95 are an example of a "computer" relating to the technique of the present disclosure.

The power feed unit 90 supplies electric power from the battery 82 to the units. In more detail, the power feed unit 90 is constituted of a direct current (DC)-to-DC converter that converts a direct-current voltage from the battery 82 to a voltage having a value according to a supply destination, a voltage stabilization circuit that stabilizes a value of the converted voltage, and the like. The connector 84 is also connected to the power feed unit 90, and in a case where the cable for wired communication is connected to the connector 84, the power feed unit 90 receives electric power from the movable radiography apparatus 11 through the connector 84 and supplies electric power from the movable radiography apparatus 11 to the units.

The communication unit 91 performs wireless communication using the antennas 83 or wired communication using the connector 84. The communication unit 91 has an inquiry function of transmitting an inquiry signal for confirming whether or not communication is established with the communication unit 26 of the movable radiography apparatus 11 as a communication partner at regular intervals. In a case where there is a response from the communication unit 26 to the inquiry signal, the communication unit 91 determines that communication is established with the communication unit 26. On the contrary, in a case where there is no response from the communication unit 26 to the inquiry signal, the communication unit 91 determines that communication is not established with the communication unit 26. An interval at which the inquiry signal is transmitted is in seconds, for example, 10 seconds.

The ROM 92 stores various programs and various kinds of data associated with various programs. The RAM 93 is a work memory on which the CPU 94 executes processing. The CPU 94 reads a program stored in the ROM 92 to the RAM 93 and executes processing according to the read program. With this, the CPU 94 integrally controls the operations of the units of the electronic cassette 10.

The pose detection sensor 87 is connected to the CPU 94. Though not shown, operation units, such as the standard pose recording button 86, are also connected to the CPU 94.

Figure 9:
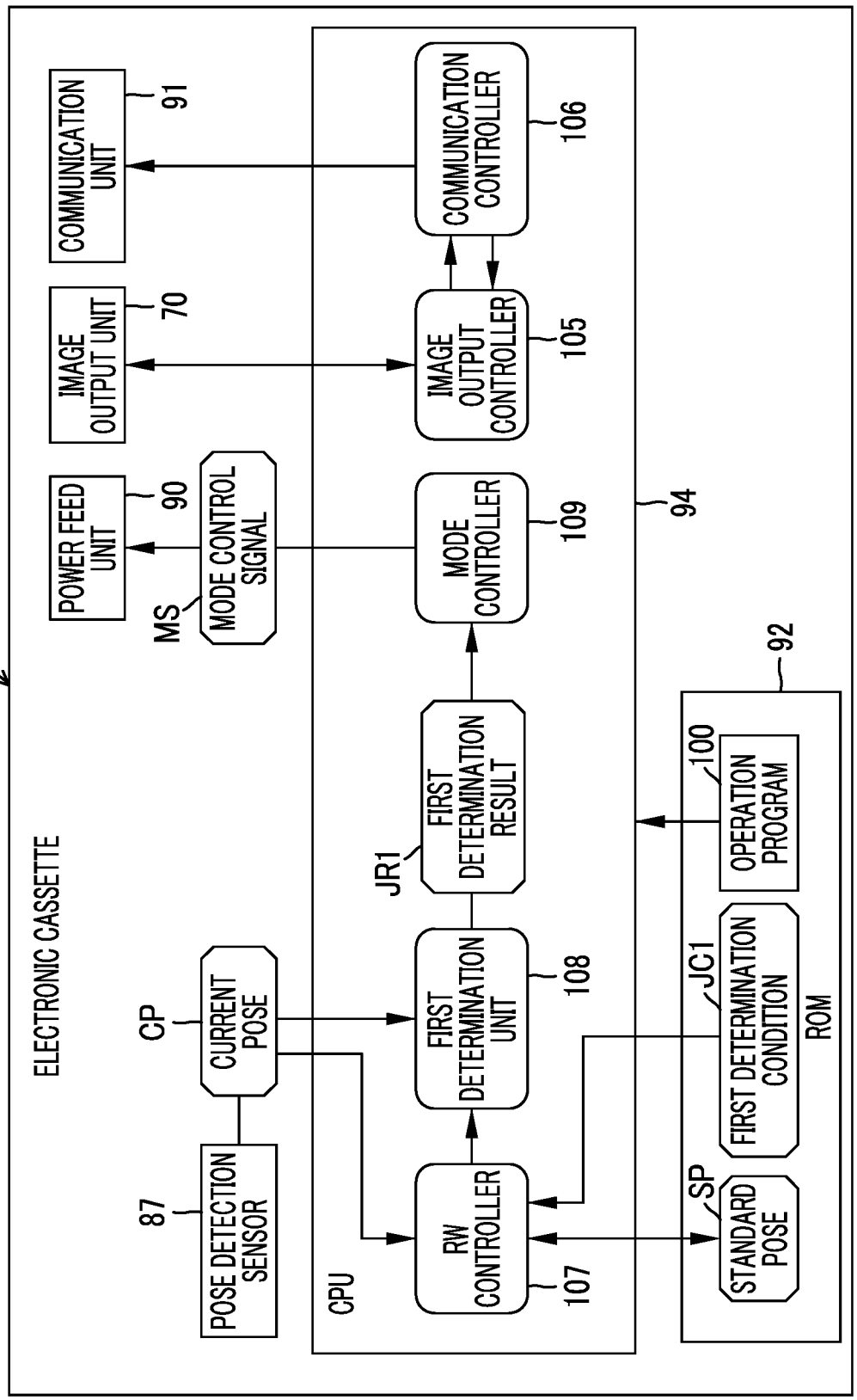
FIG. 9 is a block diagram of a CPU of the electronic cassette.

In FIG. 9, an operation program 100 is stored in the ROM 92. The operation program 100 is an example of an "operation program for an electronic cassette" related to the technique of the present disclosure. In the ROM 92, the standard pose SP and a first determination condition JC1 are stored. The first determination condition JC1 is a condition for determining whether the housing 71 is in the stored state or the taken-out state.

The CPU 94 executes the operation program 100 to function as an image output controller 105, a communication controller 106, a read write (hereinafter, abbreviated as RW) controller 107, a first determination unit 108, and a mode controller 109 in cooperation with the RAM 93 and the like.

The image output controller 105 controls the operation of the image output unit 70. For example, the image output controller 105 makes an electric charge accumulation operation to accumulate electric charge in the pixels be performed in conformity with an irradiation start timing of radiation and makes a read operation to read electric charge from the pixels be performed in conformity with an irradiation end timing of radiation. Furthermore, the image output controller 105 changes a gain to be provided to the electrical signal according to the irradiation conditions of radiation or outputs the radiographic image from the image output unit 70 to the communication controller 106.

The communication controller 106 controls the operation of the communication unit 91. For example, the communication controller 106 outputs the irradiation conditions of radiation received from the movable radiography apparatus 11 to the image output controller 105. The communication controller 106 transmits the radiographic image from the image output controller 105 to the movable radiography apparatus 11 through the communication unit 91.

The RW controller 107 reads the standard pose SP from the ROM 92. That is, the RW controller 107 is an example of a "first acquisition unit" related to the technique of the present disclosure. The ROM 92 is an example of a "storage unit" related to the technique of the present disclosure.

Furthermore, the RW controller 107 reads the first determination condition JC1 from the ROM 92. The RW controller 107 outputs the read standard pose SP and first determination condition JC1 to the first determination unit 108.

The standard pose SP and the first determination condition JC1 from the RW controller 107 and the current pose CP from the pose detection sensor 87 are input to the first determination unit 108. The first determination unit 108 determines whether the housing 71 is in the stored state or the taken-out state based on the standard pose SP and the current pose CP according to the first determination condition JC1. The first determination unit 108 outputs a determination result (hereinafter, referred to as a first determination result JR1) to the mode controller 109.

The first determination unit 108 executes low-pass filter processing (smoothing processing in 0.1 seconds or in seconds) on a detection signal representing the current pose CP from the pose detection sensor 87. After a high-frequency temporal fluctuation component is eliminated from the detection signal in this way, the first determination unit 108 performs the above-described determination.

In a case where the pose detection sensor 87 is a three-axis acceleration sensor, the current pose CP is decided by static XYZ components of a gravitational acceleration in the coordinate axes of the housing 71. Components other than an acceleration component in a gravity direction in the detection signal of the pose detection sensor 87 become an acceleration component in a case where the movable radiography apparatus 11 moves, or the like. For this reason, the first determination unit 108 eliminates the components other than the acceleration component in the gravity direction. The first determination unit 108 detects an angle with respect to the coordinate axes of the housing 71 from the acceleration component in the gravity direction after executing the low-pass filter processing on the acceleration component in the gravity direction in the detection signal as described above. The first determination unit 108 performs the above-described determination according to how the detected angle is deviated from an angle recorded as the standard pose SP in the ROM 92.

The mode controller 109 outputs, to the power feed unit 90, a mode control signal MS according to the first determination result JR1 from the first determination unit 108. With this, the mode controller 109 controls the drive mode DM.

Figure 10:
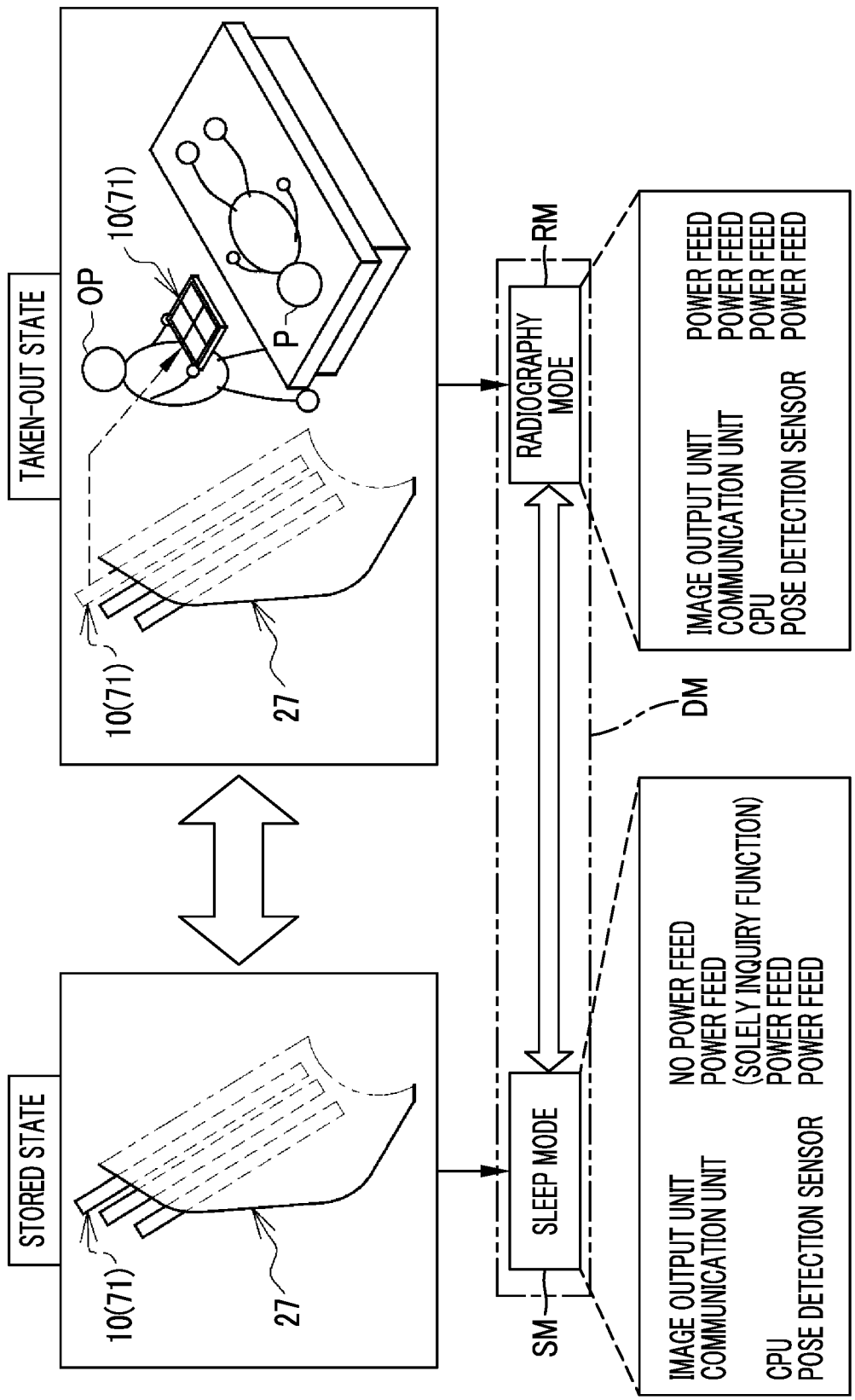
FIG. 10 is a diagram conceptually showing control of a drive mode of a mode controller.

As conceptually shown in FIG. 10, the mode controller 109 switches the drive mode DM from the sleep mode SM to the radiography mode RM in a case where the first determination unit 108 determines that the housing 71 is brought from the stored state into the taken-out state. On the other hand, the mode controller 109 switches the drive mode DM from the radiography mode RM to the sleep mode SM in a case where the first determination unit 108 determines that the housing 71 is brought from the taken-out state into the stored state.

In the radiography mode RM, the power feed unit 90 supplies electric power to the entire electronic cassette 10 including the image output unit 70, the pose detection sensor 87, the communication unit 91, the CPU 94, and the like. For this reason, in the radiography mode RM, the radiographic image can be output from the image output unit 70. In contrast, in the sleep mode SM, the power feed unit 90 supplies the same amount of electric power as in the radiography mode RM to the pose detection sensor 87 and the CPU 94, but does not supply electric power to the image output unit 70. Furthermore, the power feed unit 90 supplies electric power to the communication unit 91 by an amount needed for the inquiry function of transmitting the inquiry signal at regular intervals. For this reason, in the sleep mode SM, the radiographic image cannot be output from the image output unit 70, but power consumption is smaller than in the radiography mode RM.

In switching from the sleep mode SM to the radiography mode RM, a certain waiting time is needed until the operation of the photoelectric conversion unit of each pixel of the light detection substrate 75 is stabilized or for making the image output unit 70 output a radiographic image for offset correction.

Figure 11:
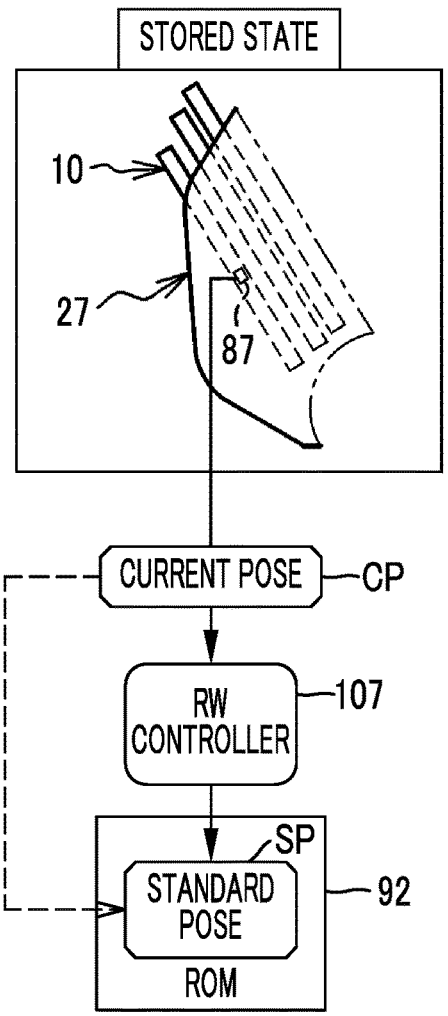
FIG. 11 is a diagram showing a manner in which a standard pose is recorded in a ROM.

As shown in FIG. 11, the RW controller 107 records the current pose CP detected by the pose detection sensor 87 in the stored state as the standard pose SP in the ROM 92. Recording of the standard pose SP in the ROM 92 with the RW controller 107 is performed, for example, through an operation of the operator OP on the standard pose recording button 86 in a case where the housing 71 is initially stored in the storage portion 27.

Figure 12:
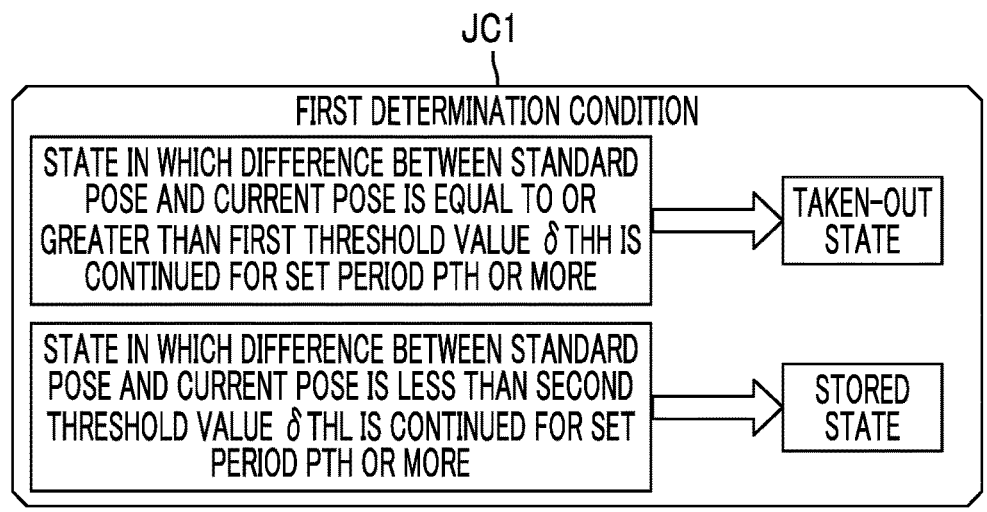
FIG. 12 is a diagram showing a first determination condition.

In FIG. 12, the first determination condition JC1 is a condition for determining that the housing 71 is brought into the taken-out state in a case where a state in which the difference between the standard pose SP and the current pose CP is equal to or greater than a preset first threshold value δTHH is continued for a preset set period PTH or more. Furthermore, the first determination condition JC1 is a condition for determining that the housing 71 is brought into the stored state in a case where a state in which the difference between the standard pose SP and the current pose CP is less than a preset second threshold value δTHL is continued for the set period PTH or more. The set period PTH may be changed between the former case and the latter case.

Figure 13:
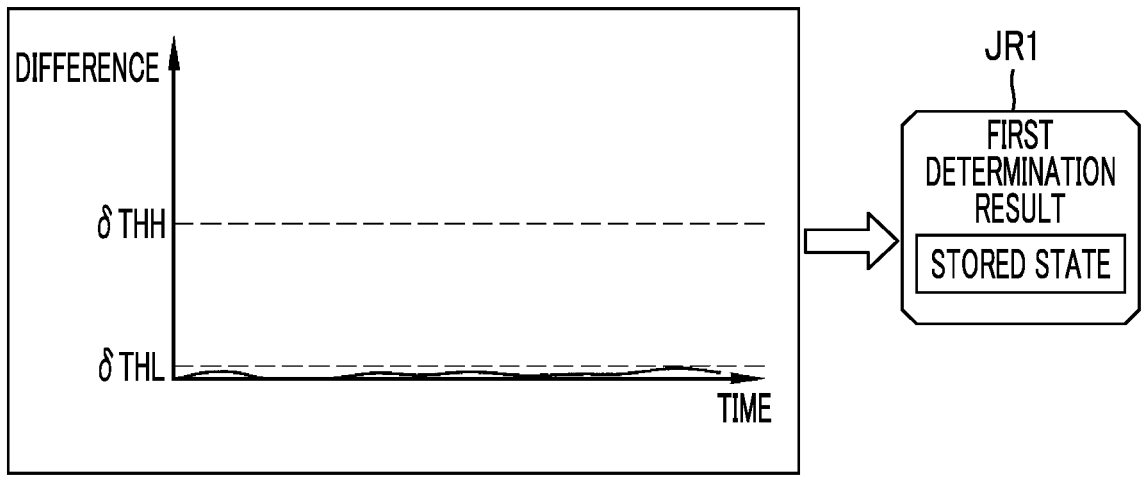
FIG. 13 is a diagram showing a first determination result in a case where a state in which a difference between a standard pose and a current pose is less than a second threshold value is continued for a set period or more.

FIGS. 13 to 18 show the first determination result JR1 in various situations in a case where the first determination condition JC1 has a content shown in FIG. 13.

First, FIG. 13 shows a case where the state in which the difference between the standard pose SP and the current pose CP is less than the second threshold value δTHL is continued for the set period PTH or more. The first determination result JR1 in this case has a content that the housing 71 is in the stored state.

Figure 14:
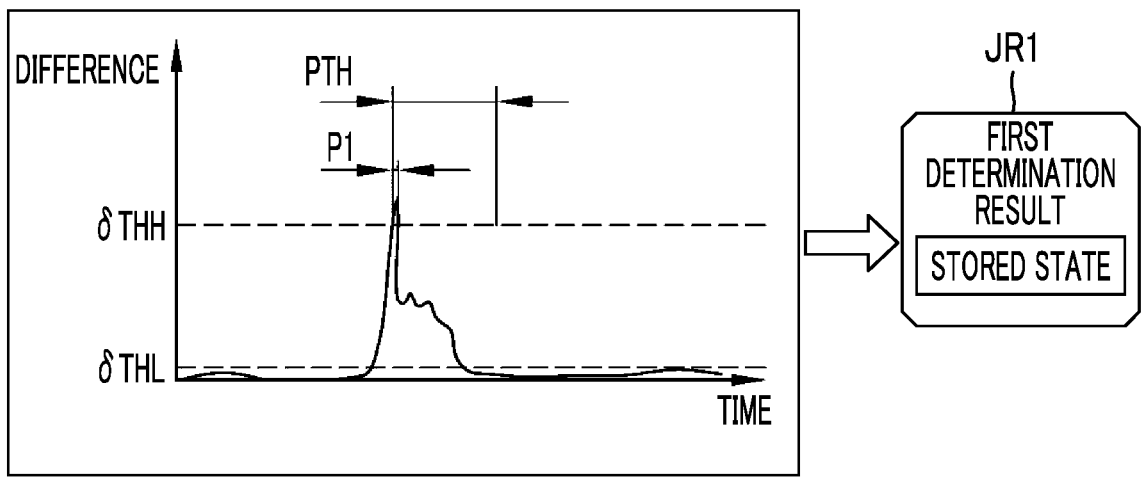
FIG. 14 is a diagram showing the first determination result in a case where a period during which the difference between the standard pose and the current pose becomes equal to or greater than a first threshold value is shorter than the set period.

FIG. 14 shows a case where the difference between the standard pose SP and the current pose CP becomes equal to or greater than the first threshold value δTHH for a period P1, but the period P1 is shorter than the set period PTH. The first determination result JR1 in this case has a content that the housing 71 is in the stored state like the case of FIG. 13.

Figure 15:
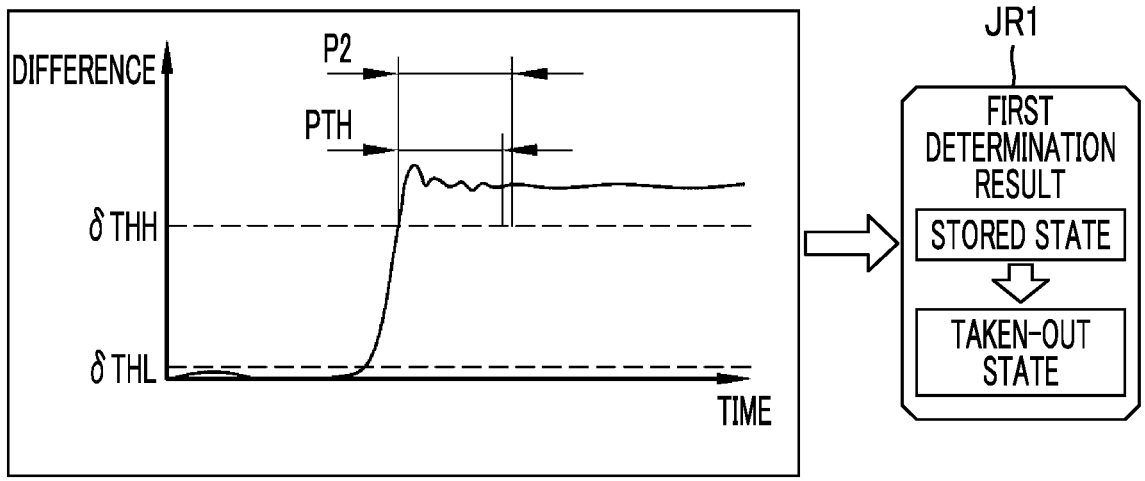
FIG. 15 is a diagram showing the first determination result in a case where the difference between the standard pose and the current pose becomes equal to or greater than the first threshold value for a period equal to or longer than the set period.

FIG. 15 shows a case where the difference between the standard pose SP and the current pose CP becomes equal to or greater than the first threshold value δTHH for a period P2 equal to or longer than the set period PTH. The first determination result JR1 in this case has a content that the housing 71 is brought from the stored state into the taken-out state.

Figure 16:
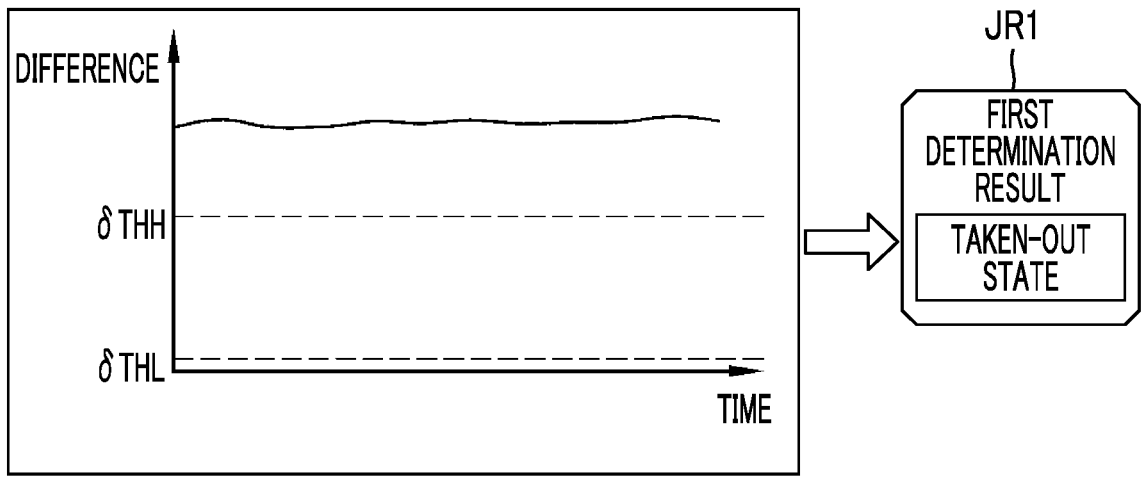
FIG. 16 is a diagram showing the first determination result in a case where a state in which the difference between the standard pose and the current pose is equal to or greater than the first threshold value is continued for the set period or more.

FIG. 16 shows a case where the state in which the difference between the standard pose SP and the current pose CP is equal to or greater than the first threshold value δTHH is continued for the set period PTH or more. The first determination result JR1 in this case has a content that the housing 71 is in the taken-out state.

Figure 17:
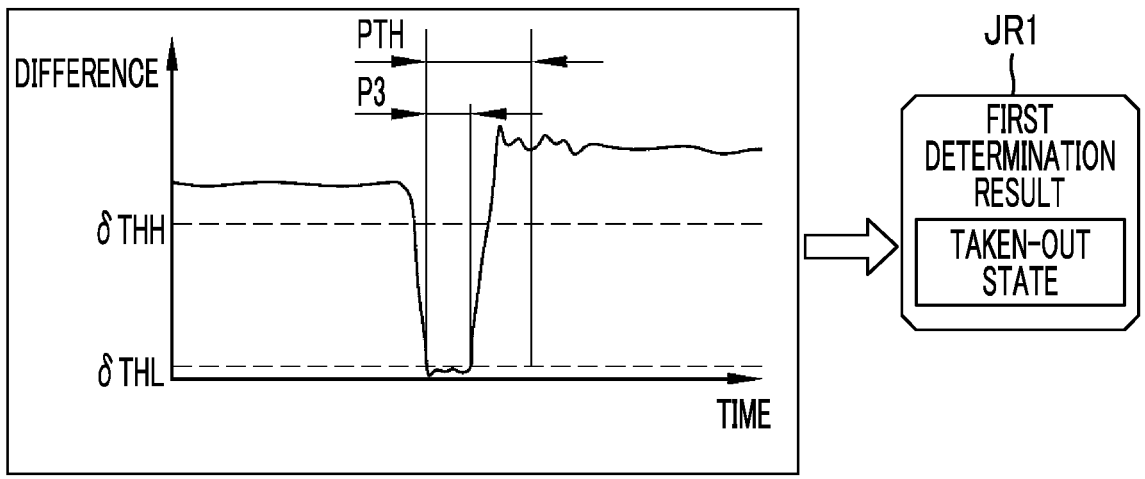
FIG. 17 is a diagram showing the first determination result in a case where a period during which the difference between the standard pose and the current pose becomes less than the second threshold value is shorter than the set period.

FIG. 17 shows a case where the difference between the standard pose SP and the current pose CP is less than the second threshold value δTHL for a period P3, but the period P3 is shorter than the set period PTH. The first determination result JR1 in this case has a content that the housing 71 is in the taken-out state like the case of FIG. 16.

Figure 18:
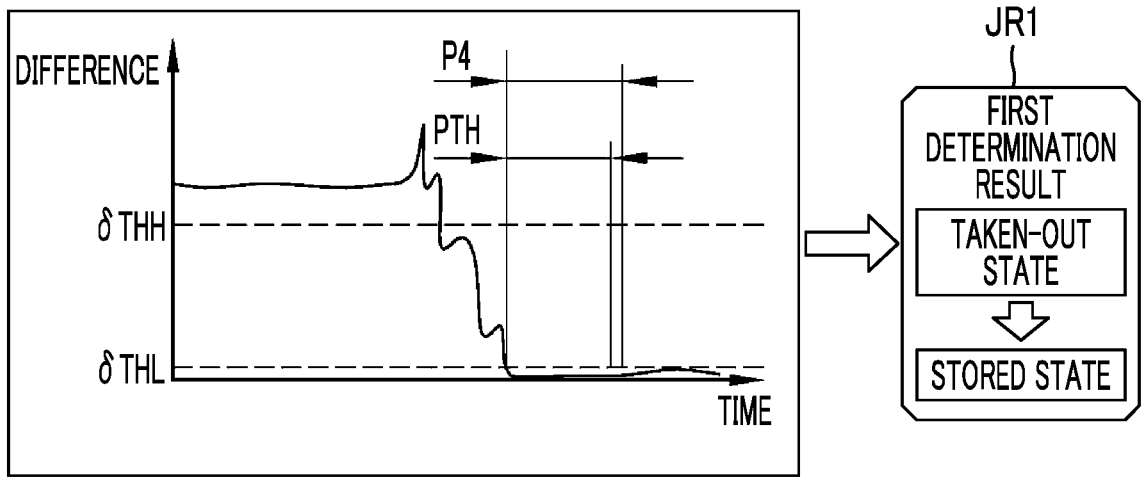
FIG. 18 is a diagram showing the first determination result in a case where the difference between the standard pose and the current pose becomes less than the second threshold value for a period equal to or longer than the set period.

FIG. 18 shows a case where the difference between the standard pose SP and the current pose CP is less than the second threshold value δTHL for a period P4 equal to or longer than the set period PTH. The first determination result JR1 in this case has a content that the housing 71 is brought from the taken-out state into the stored state.

As shown in FIG. 19, in a case where the first determination result JR1 from the first determination unit 108 has the content shown in FIG. 15 that the housing 71 is brought from the stored state into the taken-out state, the mode controller 109 outputs, to the power feed unit 90, the mode control signal MS to the effect of switching the drive mode DM from the sleep mode SM to the radiography mode RM. In contrast, as shown in FIG. 20, in a case where the first determination result JR1 from the first determination unit 108 has the content shown in FIG. 18 that the housing 71 is brought from the taken-out state into the stored state, the mode controller 109 outputs, to the power feed unit 90, the mode control signal MS to the effect of switching the drive mode DM from the radiography mode RM to the sleep mode SM.

Next, the operation according to the above-described configuration will be described referring to flowcharts shown in FIGS. 21 to 23. First, FIG. 21 is a flowchart showing a procedure of radiography with the radiography system 2 in a certain hospital room. The operator OP arrives at the hospital room along with the movable radiography apparatus 11 mounted with the electronic cassette 10 (Step ST100). After arriving at the hospital room, the operator OP operates the console table 30 of the console 25 to perform setting of the irradiation conditions and selection of the radiography menu (Step ST110).

Subsequently, the operator OP takes out the housing 71 of the electronic cassette 10 for use in radiography from the storage portion 27 (Step ST120). As the storage portion 27 is taken out in this way, as shown in FIGS. 10 and 19, the drive mode DM of the electronic cassette 10 is switched from the sleep mode SM to the radiography mode RM.

The operator OP performs pairing of the taken-out electronic cassette 10 and the movable radiography apparatus 11 (Step ST130). Pairing is processing for establishing communication between the communication unit 91 of the electronic cassette 10 for use in radiography and the communication unit 26 of the movable radiography apparatus 11.

After pairing ends, the operator OP performs positioning (Step ST140). Positioning is a work of making the patient P take a radiography pose selected on the radiography menu or setting the electronic cassette 10 on a radiography region selected on the radiography menu. Positioning is a work of operating the lock and unlock switches 33 and 42 to perform unlocking and driving the movable portions of the column portion 21, the arm portion 22, and the swing portion 57 to set the irradiation portion 23 at a position facing the front surface 76 of the electronic cassette 10 or operating the irradiation field limiter 41 to adjust the irradiation field and turning on the irradiation field lamp 43 to confirm the irradiation field. After positioning ends, the operator OP operates the irradiation switch 32 to make the radiography system 2 perform radiography (Step ST150).

After radiography ends, the operator OP stores the housing 71 in the storage portion 27 (Step ST160). As the housing 71 is stored in the storage portion 27 in this way, as shown in FIGS. 10 and 20, the drive mode DM of the electronic cassette 10 is switched from the radiography mode RM to the sleep mode SM.

The operator OP cancels pairing the communication unit 91 of the electronic cassette 10 and the communication unit 26 of the movable radiography apparatus 11 (Step ST170). Thereafter, the operator OP returns the movable portions of the column portion 21, the arm portion 22, and the swing portion 57 to the original states, stores the irradiation portion 23 at a storage position shown in FIG. 1, and then, operates the lock and unlock switches 33 and 42 to lock the movable portions (Step ST180). The operator OP departs for a next destination along with the movable radiography apparatus 11 (Step ST190). With the above, radiography with the radiography system 2 in a certain hospital room ends.

In a case where the operation program 100 is activated, as shown in FIG. 9, the CPU 94 of the electronic cassette 10 functions as the image output controller 105, the communication controller 106, the RW controller 107, the first determination unit 108, and the mode controller 109.

As shown in FIG. 22, first, the current pose CP is detected by the pose detection sensor 87 in the stored state as preliminary preparation (Step ST500). Then, as shown in FIG. 11, the detected current pose CP in the stored state is recorded as the standard pose SP in the ROM 92 by the RW controller 107 (Step ST510).

Figure 23:
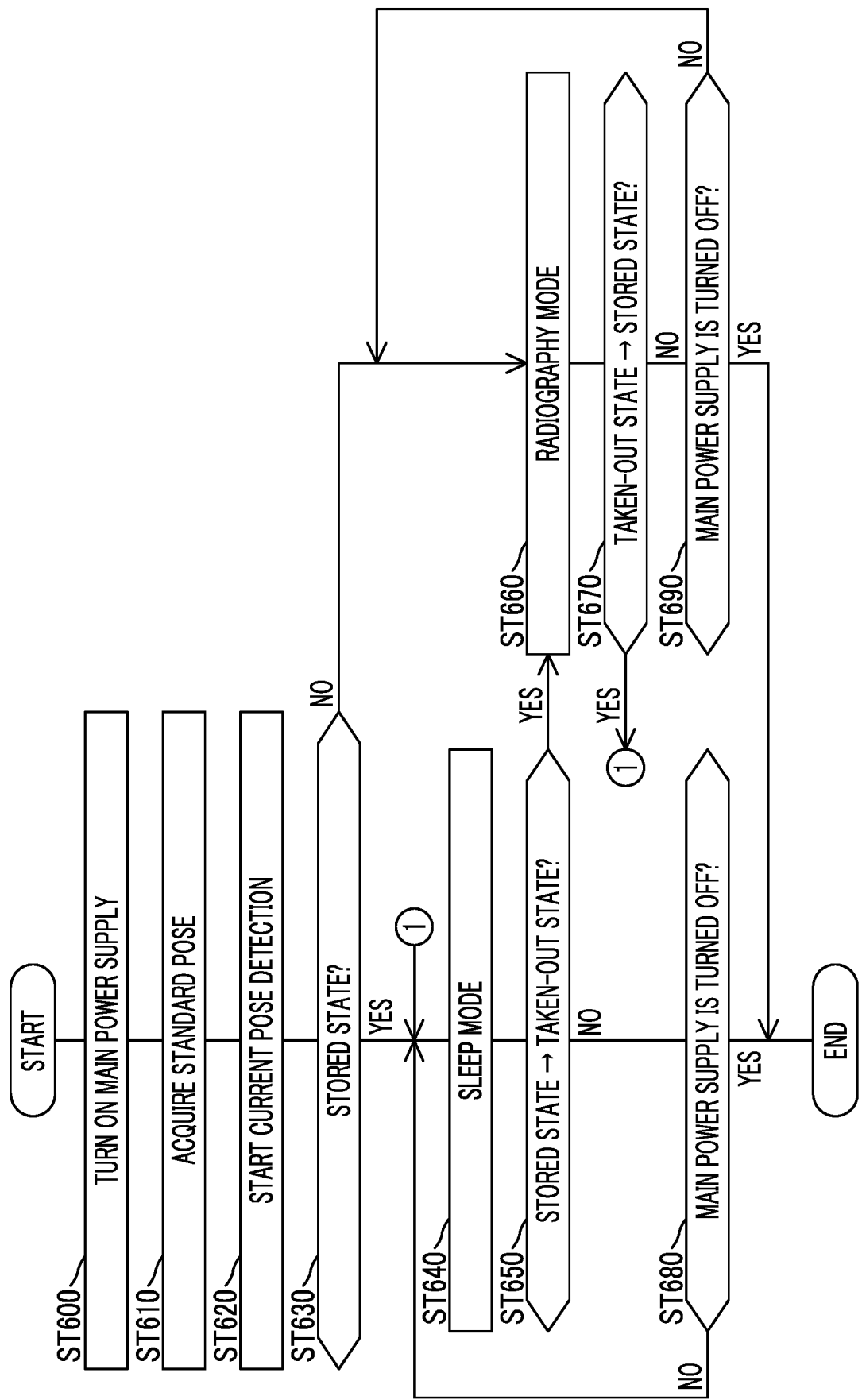
FIG. 23 is a flowchart showing a processing procedure of the electronic cassette.

In FIG. 23, in the electronic cassette 10, in a case where the main power supply is turned on (Step ST600), the standard pose SP is read from the ROM 92 by the RW controller 107 (Step ST610). Furthermore, detection of the current pose CP is started by the pose detection sensor 87 (Step ST620). The standard pose SP is output from the RW controller 107 to the first determination unit 108. The current pose CP is output from the pose detection sensor 87 to the first determination unit 108. Step ST610 is an example of a "first acquisition step" related to the technique of the present disclosure.

In the first determination unit 108, as shown in FIGS. 13 to 18, determination is made whether the housing 71 is in the stored state or the taken-out state based on the standard pose SP from the RW controller 107 and the current pose CP from the pose detection sensor 87. The determination is performed according to the first determination condition JC1 shown in FIG. 12. The first determination result JR1 of the determination is output from the first determination unit 108 to the mode controller 109.

As shown in FIG. 15, in a case where the state in which the difference between the standard pose SP and the current pose CP is equal to or greater than the preset first threshold value δTHH is continued for the preset set period PTH or more, the first determination unit 108 determines that the housing 71 is brought into the taken-out state. In contrast, as shown in FIG. 14, in a case where the period during which the difference between the standard pose SP and the current pose CP becomes equal to or greater than the first threshold value δTHH is shorter than the set period PTH, determination is not made that the housing 71 is brought into the taken-out state. Accordingly, it is possible to restrain erroneous determination that the housing 71 is brought into the taken-out state in a case where the difference between the standard pose SP and the current pose CP temporarily becomes equal to or greater than the first threshold value δTHH due to unexpected noise, such as load noise, called a level difference.

Furthermore, as shown in FIG. 18, in a case where the state in which the difference between the standard pose SP and the current pose CP is less than the preset second threshold value δTHL is continued for the set period PTH or more, the first determination unit 108 determines that the housing 71 is brought into the stored state. In contrast, as shown in FIG. 17, a period during which the difference between the standard pose SP and the current pose CP becomes less than the second threshold value δTHL is shorter than the set period PTH, determination is not made that the housing 71 is brought into the stored state. Accordingly, it is possible to restrain erroneous determination that the housing 71 is brought into the stored state in a case where the difference between the standard pose SP and the current pose CP becomes less than the second threshold value δTHL due to unexpected noise or since the same pose as in the stored state is unexpectedly taken during positioning.

As shown in FIGS. 13 and 14, in a case of the first determination result JR1 that the housing 71 is in the stored state (in Step ST630, YES), the drive mode DM is set to the sleep mode SM by the mode controller 109 (Step ST640). In a state of the sleep mode SM, as shown in FIG. 15, in a case where the first determination result JR1 has the content that the housing 71 is brought from the stored state into the taken-out state (in Step ST650, YES), as shown in FIG. 19, the mode control signal MS to the effect of switching the drive mode DM from the sleep mode SM to the radiography mode RM is output from the mode controller 109 to the power feed unit 90. With this, the drive mode DM is switched to the radiography mode RM (Step ST660). That is, the drive mode DM of the electronic cassette 10 is switched from the sleep mode SM to the radiography mode RM in a case where the housing 71 is taken out from the storage portion 27.

As shown in FIGS. 16 and 17, in a case of the first determination result JR1 that the housing 71 is in the taken-out state (in Step ST630, NO), the drive mode DM is set to the radiography mode RM by the mode controller 109 (Step ST660). In a state of the radiography mode RM, as shown in FIG. 18, in a case where the first determination result JR1 has the content that the housing 71 is brought from the taken-out state into the stored state (in Step ST670, YES), as shown in FIG. 20, the mode control signal MS to the effect of switching the drive mode DM from the radiography mode RM to the sleep mode SM is output from the mode controller 109 to the power feed unit 90. With this, the drive mode DM is switched to the sleep mode SM (Step ST640). That is, the drive mode DM of the electronic cassette 10 is switched from the radiography mode RM to the sleep mode SM in a case where the housing 71 is stored in the storage portion 27.

A series of processing described above is continuously repeated until the main power supply of the electronic cassette 10 is turned off (in Step ST680 or Step ST690, YES). Steps ST630, ST650, and ST670 are an example of a "first determination step" related to the technique of the present disclosure. Steps ST640 and ST660 are an example of a "mode control step" related to the technique of the present disclosure.

As described above, the electronic cassette 10 comprises the RW controller 107, the first determination unit 108, and the mode controller 109. The RW controller 107 reads and acquires, from the ROM 92, the standard pose SP as the pose of the housing in the stored state in which the housing 71 is stored in the storage portion 27 of the movable radiography apparatus 11. The first determination unit 108 determines whether the housing 71 is in the stored state or the taken-out state in which the housing 71 is taken out from the storage portion 27 based on the standard pose SP and the current pose CP as the current pose of the housing 71 from the pose detection sensor 87. The mode controller 109 switches the drive mode DM from the sleep mode SM to the radiography mode RM in a case where the first determination unit 108 determines that the housing is brought from the stored state into the taken-out state.

It is possible to surely determine whether the current pose CP from the pose detection sensor 87 changes as the housing 71 is stored in the storage portion 27 and is moved along with the movable radiography apparatus 11 or changes as the housing 71 is lifted up by the operator OP. In addition, it is possible to surely determine whether the current pose CP from the pose detection sensor 87 changes as the housing 71 is taken out from the storage portion 27 or changes as the housing 71 is carried after taken out from the storage portion 27. Accordingly, it is possible to surely perform the control of the drive mode DM in patrol radiography using the movable radiography apparatus 11.

In JP2009-175104A, the contact detection sensor is provided in order to switch the drive mode DM from the sleep mode SM to the radiography mode RM, in the technique of the present disclosure, the contact detection sensor is not needed. Accordingly, it is possible to switches the drive mode DM from the sleep mode SM to the radiography mode RM in patrol radiography using the movable radiography apparatus 11 without restrictions on use. Furthermore, since the contact detection sensor is not needed, it is possible to reduce component cost.

As described above, some time is needed for switching from the sleep mode SM to the radiography mode RM. For this reason, in a case where the drive mode DM is switched from the sleep mode SM to the radiography mode RM immediately before radiography, a certain waiting time is needed until the drive mode DM becomes the radiography mode RM. However, in the technique of the present disclosure, the drive mode DM of the electronic cassette 10 is switched from the sleep mode SM to the radiography mode RM in a case where the housing 71 is taken out from the storage portion 27. Accordingly, before radiography is performed, the drive mode DM is reliably switched to the radiography mode RM, and a waiting time is not generated.

Furthermore, the drive mode DM of the electronic cassette 10 is switched from the radiography mode RM to the sleep mode SM in a case where the housing 71 is stored in the storage portion 27. Accordingly, it is possible to suppress wasteful power consumption.

The electronic cassette 10 is incorporated with a ROM 92 that stores the standard pose SP. In a case where the standard pose SP is stored in a storage unit of a device other than the electronic cassette 10, and the standard pose SP is acquired from the storage unit of the device, it is not possible to output even the first determination result JR1 in a case where connection of the device is disconnected. In contrast, in the technique of the present disclosure, it is possible to complete processing in a closed system of the electronic cassette 10 alone.

As the ROM 92 that stores the standard pose SP is incorporated in the electronic cassette 10, in a case where the electronic cassette 10 that is used in a certain movable radiography apparatus 11 is used in another movable radiography apparatus 11, it is possible to simply rewrite the standard pose SP to that of the other movable radiography apparatus 11.

A case where one electronic cassette 10 is used in a plurality of movable radiography apparatuses 11 is also considered. In this case, the standard pose SP of each of a plurality of movable radiography apparatuses 11 may be stored in the ROM 92, and in radiography, the operator OP is made to select the standard pose SP corresponding to the movable radiography apparatus 11 to be used.

The standard pose SP may be opened, for example, on a homepage or the like of a manufacturer of the movable radiography apparatus 11, and may be freely downloaded to the electronic cassette 10.

The drive mode DM may be started from the sleep mode SM regardless of the current pose CP in a case where the main power supply is turned on.

The movable radiography apparatus 11 is not limited to an electric assistant type. The movable radiography apparatus 11 may be of a type in which the operator OP pushes and moves the movable radiography apparatus using human power.

Second Embodiment

In a second embodiment shown in FIGS. 24 to 30, operation state information SI indicating an operation state of the movable radiography apparatus 11 is acquired, and determination is made whether or not the movable radiography apparatus 11 is in a radiography preparation state based on the operation state information SI. Then, the drive mode DM is controlled based on a determination result.

Figure 24:
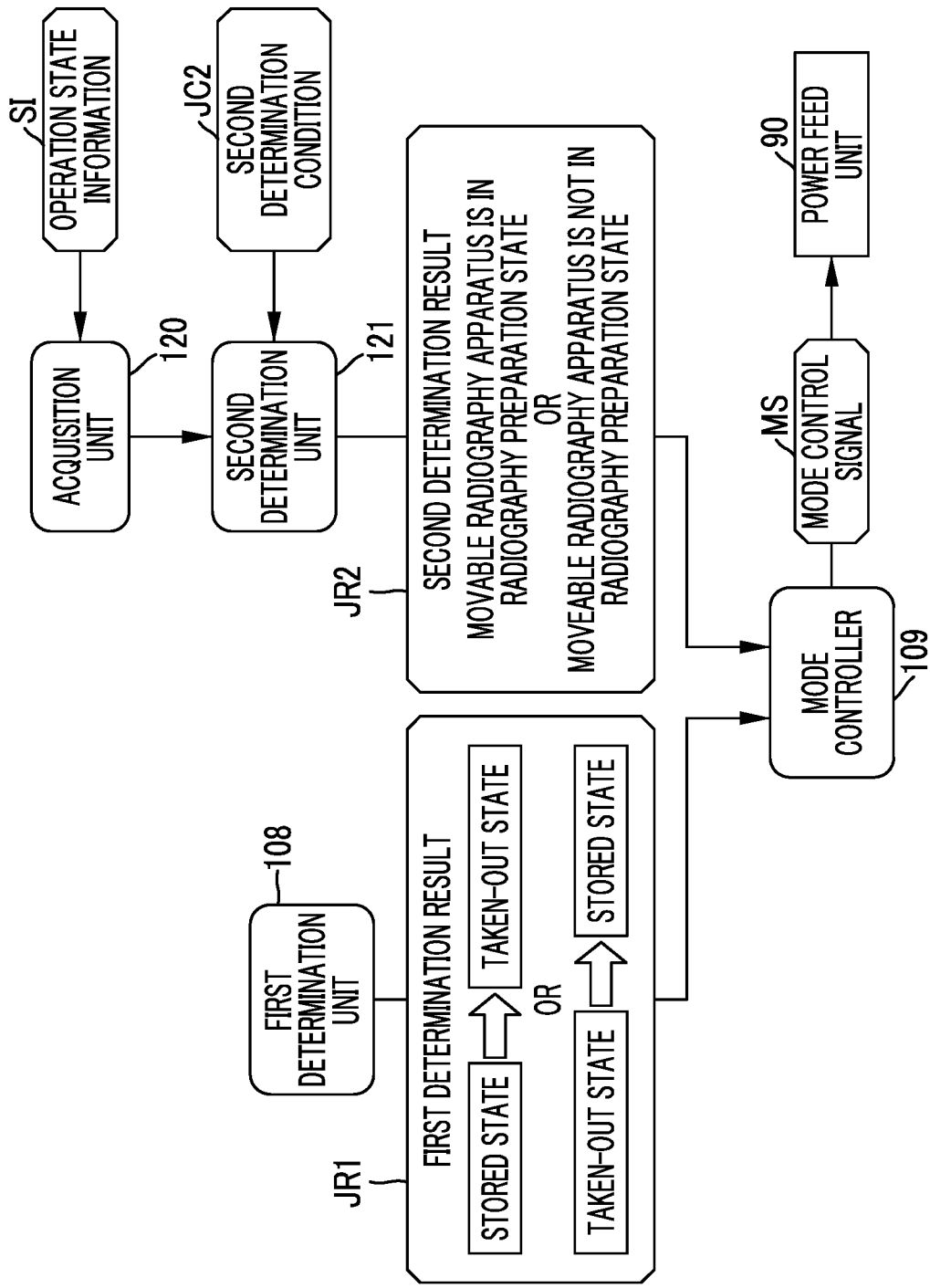
FIG. 24 is a diagram showing a second embodiment in which operation state information indicating an operation state of a movable radiography apparatus is acquired and determination is made whether or not the movable radiography apparatus is in a radiography preparation state based on the operation state information.

In FIG. 24, the CPU 94 of the electronic cassette 10 of the second embodiment functions as an acquisition unit 120 and a second determination unit 121, in addition to the processing units 105 to 109 (in FIG. 24, only the first determination unit 108 and the mode controller 109 are shown) of the above-described first embodiment. The acquisition unit 120 acquires the operation state information SI indicating the operation state of the movable radiography apparatus 11. That is, the acquisition unit 120 is an example of a "second acquisition unit" related to the technique of the present disclosure. The acquisition unit 120 outputs the acquired operation state information SI to the second determination unit 121.

The second determination unit 121 determines whether or not the movable radiography apparatus 11 is in the radiography preparation state based on operation state information SI according to a second determination condition JC2. The second determination unit 121 outputs a determination result (hereinafter, referred to as a second determination result JR2) to the mode controller 109. The second determination result has either of a content that the movable radiography apparatus 11 is in the radiography preparation state or a content that the movable radiography apparatus 11 is not in the radiography preparation state. The second determination condition JC2 is stored in the ROM 92 like the first determination condition JC1.

As in the above-described first embodiment, the first determination result JR1 is input from the first determination unit 108 to the mode controller 109. The mode controller 109 controls the drive mode DM based on the first determination result JR1 and the second determination result JR2 from the second determination unit 121.

Figure 25:
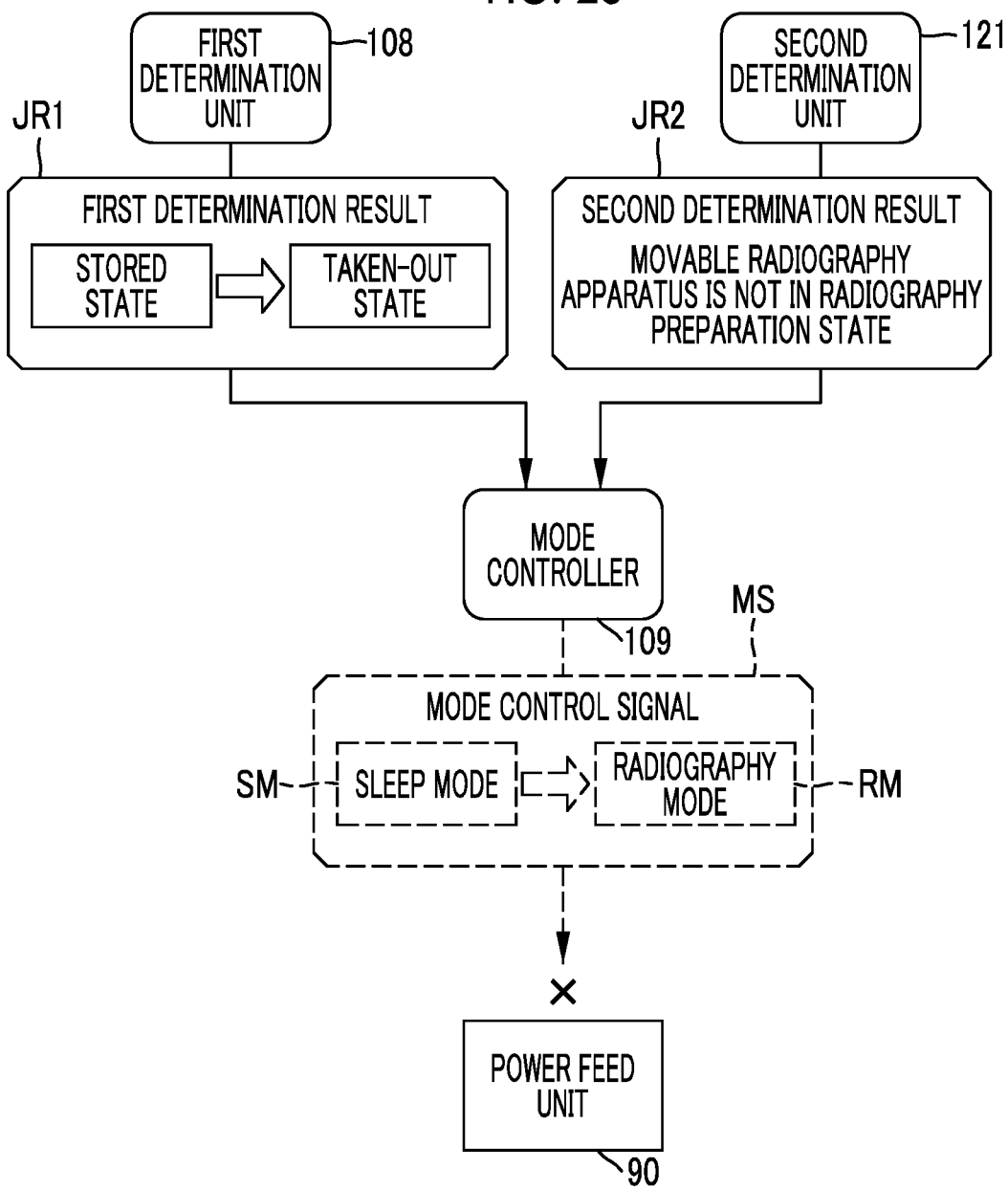
FIG. 25 is a diagram showing a case where a first determination unit determines that a housing is brought from a stored state into a taken-out state, and a second determination unit determines that the movable radiography apparatus is not in the radiography preparation state.

As shown in FIG. 25, in a case where the first determination result JR1 from the first determination unit 108 has the content that the housing 71 is brought from the stored state into the taken-out state, and the second determination result JR2 from the second determination unit 121 has the content that the movable radiography apparatus 11 is not in the radiography preparation state, the mode controller 109 does not output, to the power feed unit 90, the mode control signal MS to the effect of switching the drive mode DM from the sleep mode SM to the radiography mode RM. That is, in a case where the first determination unit 108 determines that the housing 71 is brought from the stored state into the taken-out state, and the second determination unit 121 determines that the movable radiography apparatus 11 is not in the radiography preparation state, the mode controller 109 does not perform switching from the sleep mode SM to the radiography mode RM.

Figure 26:
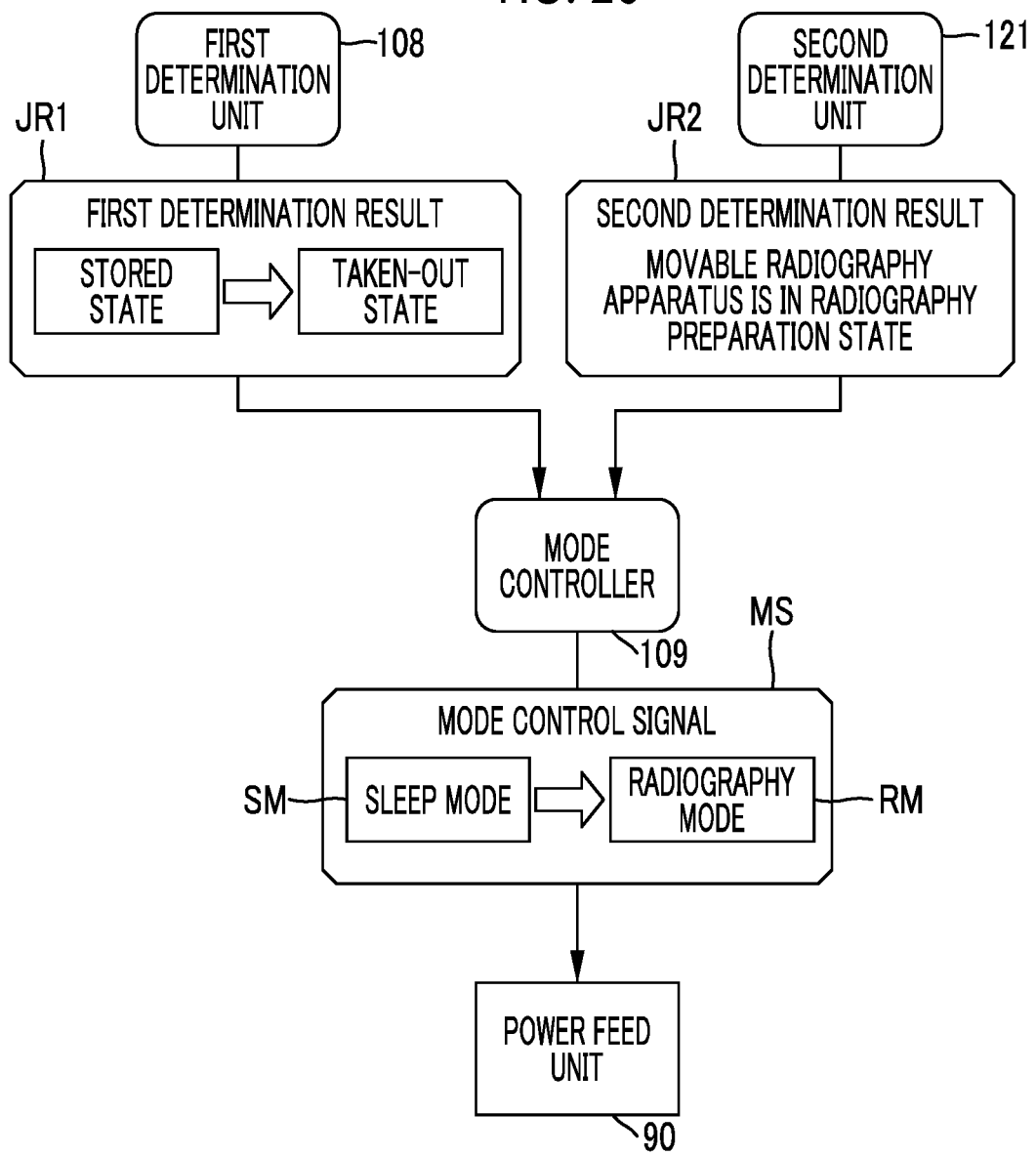
FIG. 26 is a diagram showing a case where the first determination unit determines that the housing is brought from the stored state into the taken-out state, and the second determination unit determines that the movable radiography apparatus is in the radiography preparation state.

In contrast, as shown in FIG. 26, in a case where the first determination result JR1 from the first determination unit 108 has the content that the housing 71 is brought from the stored state into the taken-out state, and the second determination result JR2 from the second determination unit 121 has the content that the movable radiography apparatus 11 is in the radiography preparation state, the mode controller 109 outputs, to the power feed unit 90, the mode control signal MS to the effect of switching the drive mode DM from the sleep mode SM to the radiography mode RM. That is, in a case where the first determination unit 108 determines that the housing 71 is brought from the stored state into the taken-out state, and the second determination unit 121 determines that the movable radiography apparatus 11 is in the radiography preparation state, the mode controller 109 performs switching from the sleep mode SM to the radiography mode RM.

Figure 27:
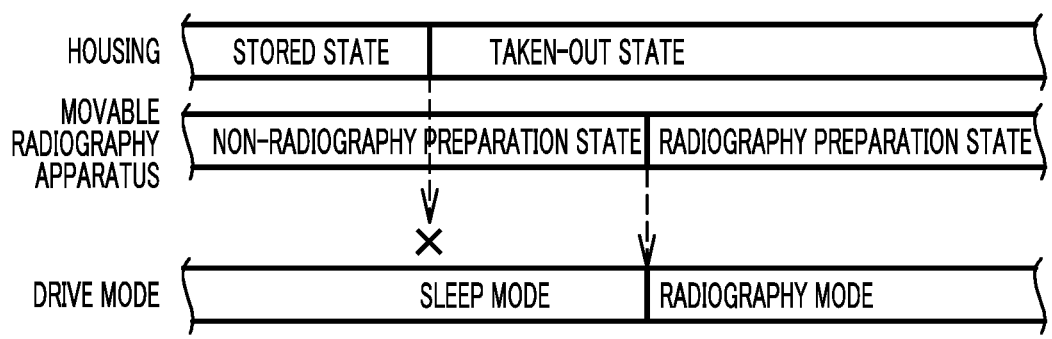
FIG. 27 is a timing chart of mode control described in FIGS. 25 and 26.

FIG. 27 is a timing chart of mode control described referring to FIGS. 25 and 26. The mode controller 109 maintains the drive mode DM as the sleep mode SM while the movable radiography apparatus 11 is not in the radiography preparation state (in FIG. 27, referred to a "non-radiography preparation state"; the same applies to FIG. 30) even after the housing 71 is brought from the stored state into the taken-out state. Then, in a case where the movable radiography apparatus 11 is brought into the radiography preparation state, the mode controller 109 switches the drive mode DM to the radiography mode RM.

Figure 28:
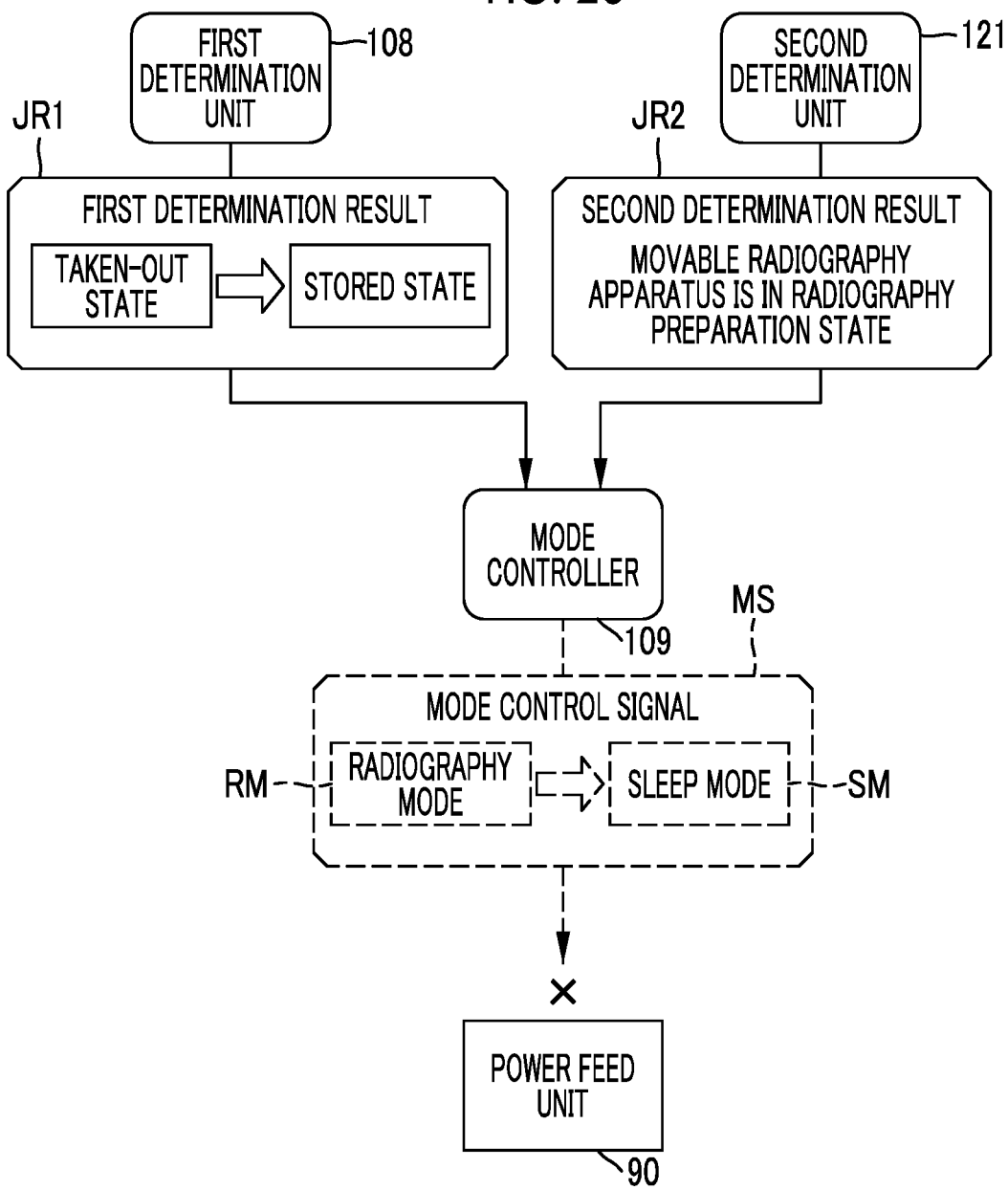
FIG. 28 is a diagram showing a case where the first determination unit determines that the housing is brought from the taken-out state into the stored state, and the second determination unit determines that the movable radiography apparatus is in the radiography preparation state.

As shown in FIG. 28, in a case where the first determination result JR1 from the first determination unit 108 has the content that the housing 71 is brought from the taken-out state into the stored state, and the second determination result JR2 from the second determination unit 121 has the content that the movable radiography apparatus 11 is in the radiography preparation state, the mode controller 109 does not output, to the power feed unit 90, the mode control signal MS to the effect of switching the drive mode DM from the radiography mode RM to the sleep mode SM. That is, in a case where the first determination unit 108 determines that the housing 71 is brought from the taken-out state into the stored state, and the second determination unit 121 determines that the movable radiography apparatus 11 is in the radiography preparation state, the mode controller 109 does not perform switching from the radiography mode RM to the sleep mode SM.

Figure 29:
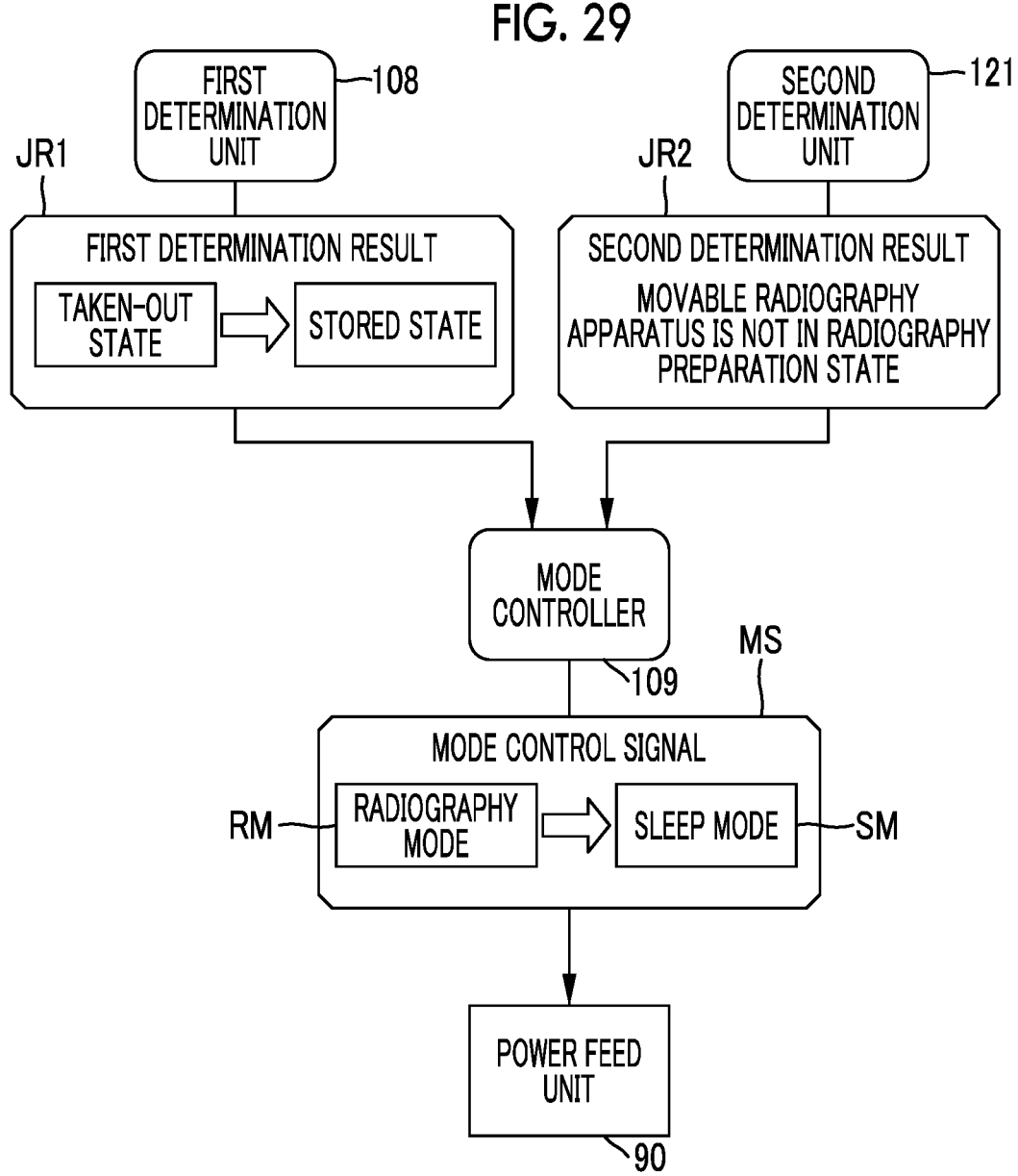
FIG. 29 is a diagram showing a case where the first determination unit determines that the housing is brought from the taken-out state into the stored state, and the second determination unit determines that the movable radiography apparatus is not in the radiography preparation state.

In contrast, as shown in FIG. 29, in a case where the first determination result JR1 from the first determination unit 108 has the content that the housing 71 is brought from the taken-out state into the stored state, and the second determination result JR2 from the second determination unit 121 has the content that the movable radiography apparatus 11 is not in the radiography preparation state, the mode controller 109 outputs, to the power feed unit 90, the mode control signal MS to the effect of switching the drive mode DM from the radiography mode RM to the sleep mode SM. That is, in a case where the first determination unit 108 determines that the housing 71 is brought from the taken-out state into the stored state, and the second determination unit 121 determines that the movable radiography apparatus 11 is not in the radiography preparation state, the mode controller 109 performs switching from the radiography mode RM to the sleep mode SM.

Figure 30:
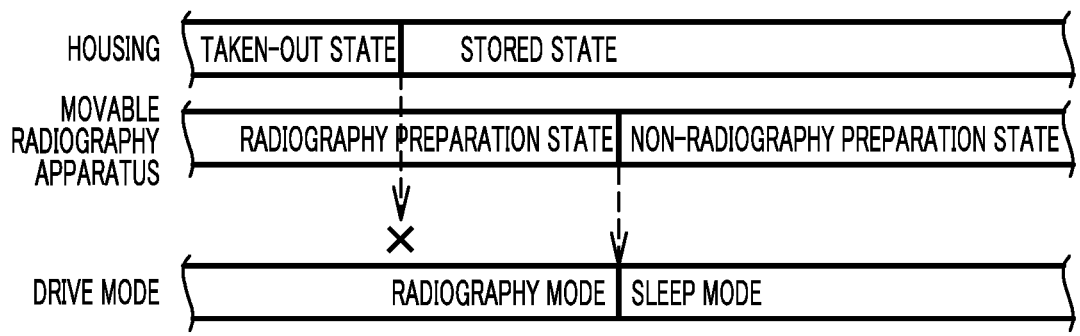
FIG. 30 is a timing chart of mode control described in FIGS. 28 and 29.

FIG. 30 is a timing chart of mode control described referring to FIGS. 28 and 29. The mode controller 109 maintains the drive mode DM as the radiography mode RM while the movable radiography apparatus 11 is in the radiography preparation state even after housing 71 is brought from the taken-out state into the stored state. Then, in a case where the movable radiography apparatus 11 is not in the radiography preparation state, the mode controller 109 switches the drive mode DM to the sleep mode SM.

In this way, in the second embodiment, as shown in FIG. 24, the acquisition unit 120 acquires the operation state information SI indicating the operation state of the movable radiography apparatus 11. The second determination unit 121 determines whether or not the movable radiography apparatus 11 is in the radiography preparation state based on the operation state information SI.

As shown in FIG. 25, in a case where the first determination unit 108 determines that the housing 71 is brought from the stored state into the taken-out state, and the second determination unit 121 determines that the movable radiography apparatus 11 is not in the radiography preparation state, the mode controller 109 does not perform switching from the sleep mode SM to the radiography mode RM. As shown in FIG. 26, in a case where the first determination unit 108 determines that the housing 71 is brought from the stored state into the taken-out state, and the second determination unit 121 determines that the movable radiography apparatus 11 is in the radiography preparation state, the mode controller 109 performs switching from the sleep mode SM to the radiography mode RM. Accordingly, the drive mode DM is restrained from being easily switched to the radiography mode RM even though the movable radiography apparatus 11 is not in the radiography preparation state, and it is possible to further suppress wasteful power consumption.

As shown in FIG. 28, in a case where the first determination unit 108 determines that the housing 71 is brought from the taken-out state into the stored state, and the second determination unit 121 determines that the movable radiography apparatus 11 is in the radiography preparation state, the mode controller 109 does not perform switching from the radiography mode RM to the sleep mode SM. In contrast, as shown in FIG. 29, in a case where the first determination unit 108 determines that the housing 71 is brought from the taken-out state into the stored state, and the second determination unit 121 determines that the movable radiography apparatus 11 is not in the radiography preparation state, the mode controller 109 performs switching from the radiography mode RM to the sleep mode SM. Accordingly, it is possible to restrain the drive mode DM from being easily switched to the sleep mode SM in a case where there is no immediate appropriate place for the electronic cassette 10 that is to be used in radiography, and the housing 71 of the electronic cassette 10 is temporarily stored in the storage portion 27, or the like. In a case where the drive mode is switched to the sleep mode SM once, a considerable time is needed until the drive mode DM is set to the radiography mode RM again, thereby hindering smooth progress of radiography; however, such a risk can be eliminated.

Third to fifth embodiments described below show specific examples of the operation state information SI and the second determination condition JC2 of the above-described second embodiment.

Third Embodiment

In a third embodiment shown in FIGS. 31 to 34, information indicating whether or not the irradiation portion 23 is in a use state is set as the operation state information SI.

Figure 31:
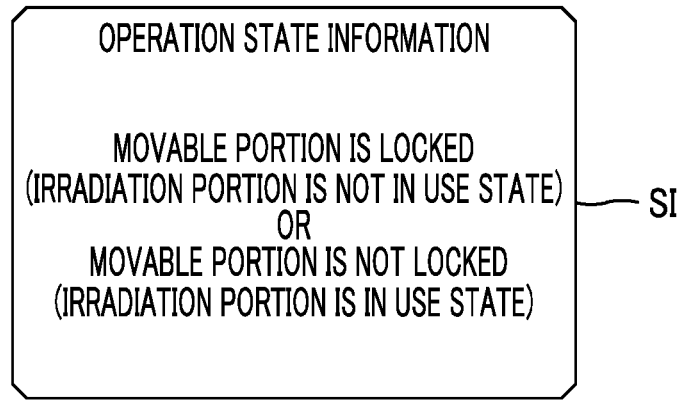
FIG. 31 is a diagram showing operation state information of a third embodiment.

As shown in FIG. 31, the operation state information SI of the embodiment has either of a content that the movable portions of the column portion 21, the arm portion 22, and the swing portion 57 are locked (the irradiation portion 23 is not in the use state) or a content that the movable portions are not locked (the irradiation portion 23 is in the use state). The acquisition unit 120 acquires, from the movable radiography apparatus 11, the operation state information SI indicating whether or not the movable portions are locked and outputs the operation state information SI to the second determination unit 121. The operation state information SI indicating whether or not the movable portions are locked is an example of "information indicating whether or not the irradiation portion is in the use state" related to the technique of the present disclosure.

Figure 32:
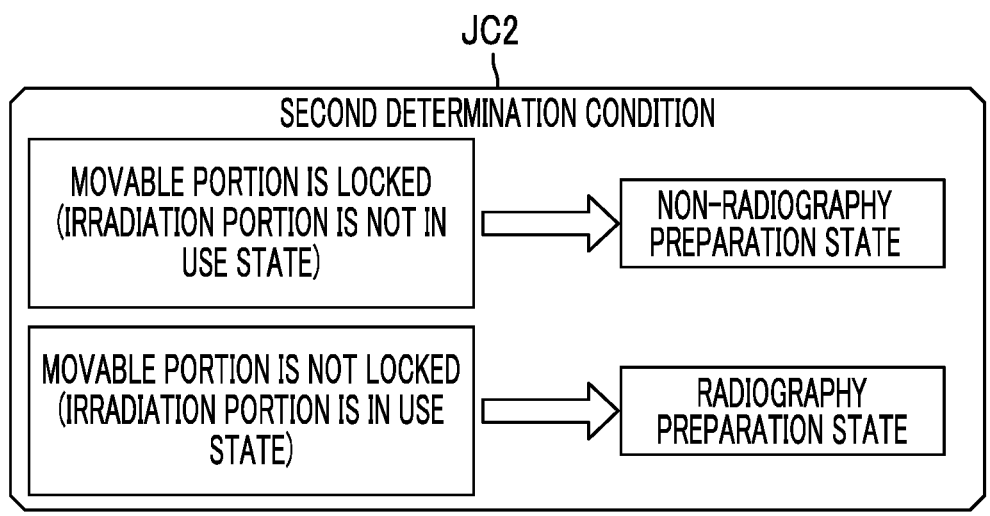
FIG. 32 is a diagram showing a second determination condition of the third embodiment.

As shown in FIG. 32, the second determination condition JC2 of the embodiment is a condition for determining that the irradiation portion 23 is not in the use state and the movable radiography apparatus 11 is not in the radiography preparation state in a case where the movable portions are locked. Furthermore, the second determination condition JC2 is a condition for determining that the irradiation portion 23 is in the use state and the movable radiography apparatus 11 is in the radiography preparation state in a case where the movable portions are not locked. The second determination unit 121 determines whether or not the movable radiography apparatus 11 is in the radiography preparation state according to the second determination condition JC2.

Figure 33:
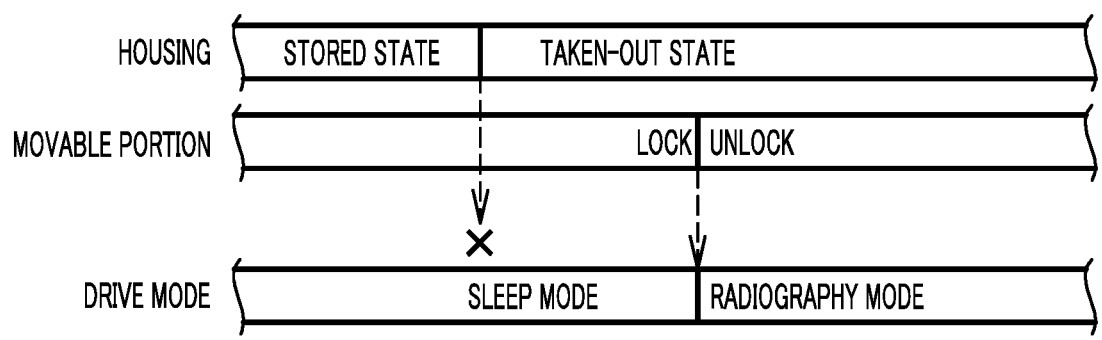
FIG. 33 is a timing chart of mode control of the third embodiment.

In a case of the operation state information SI and the second determination condition JC2, as shown in FIG. 33, the mode controller 109 maintains the drive mode DM as the sleep mode SM while the movable portions are locked even after the housing 71 is brought from the stored state into the taken-out state. Then, in a case where the movable portions are unlocked, the mode controller 109 switches the drive mode DM to the radiography mode RM.

Figure 34:
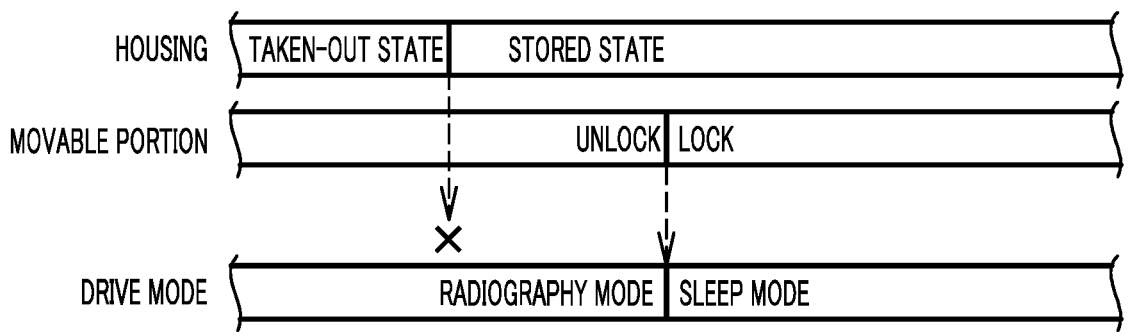
FIG. 34 is a timing chart of mode control of the third embodiment.

Furthermore, as shown in FIG. 34, the mode controller 109 maintains the drive mode DM as the radiography mode RM while the movable portions are unlocked even after the housing 71 is brought from the taken-out state into the stored state. Then, in a case where the movable portions are locked, the mode controller 109 switches the drive mode DM to the sleep mode SM.

In this way, in the third embodiment, the acquisition unit 120 acquires the operation state information SI indicating whether or not the movable portions are locked as information shown in FIG. 31 indicating whether or not the irradiation portion 23 is in the use state. According to the second determination condition JC2 shown in FIG. 32, the second determination unit 121 determines that the irradiation portion 23 is not in the use state and the movable radiography apparatus 11 is not in the radiography preparation state in a case where the movable portions are locked, and determines that the irradiation portion 23 is in the use state and the movable radiography apparatus 11 is in the radiography preparation state in a case where the movable portions are not locked.

As shown in FIG. 33, in a case where the first determination unit 108 determines that the housing 71 is brought from the stored state into the taken-out state, and the operation state information SI has the content that the irradiation portion 23 is not in the use state (the movable portions are locked), and the second determination unit 121 determines that the movable radiography apparatus 11 is not in the radiography preparation state, the mode controller 109 does not perform switching from the sleep mode SM to the radiography mode RM. In contrast, in a case where the first determination unit 108 determines that the housing 71 is brought from the stored state into the taken-out state, the operation state information SI has the content that the irradiation portion 23 is in the use state (the movable portions are not locked), and the second determination unit 121 determines that the movable radiography apparatus 11 is in the radiography preparation state, the mode controller 109 performs switching from the sleep mode SM to the radiography mode RM. Accordingly, the drive mode DM is restrained from being easily switched to the radiography mode RM although the movable portions are locked and the movable radiography apparatus 11 is not in the radiography preparation state, and it is possible to further suppress wasteful power consumption.

Furthermore, as shown in FIG. 34, in a case where the first determination unit 108 determines that the housing 71 is brought from the taken-out state into the stored state, and the operation state information SI has the content that the irradiation portion 23 is in the use state (the movable portions are not locked), and the second determination unit 121 determines that the movable radiography apparatus 11 is in the radiography preparation state, the mode controller 109 does not perform switching from the radiography mode RM to the sleep mode SM. In contrast, in a case where the first determination unit 108 determines that the housing 71 is brought from the taken-out state into the stored state, the operation state information SI has the content that the irradiation portion 23 is not in the use state (the movable portions are locked), and the second determination unit 121 determines that the movable radiography apparatus 11 is not in the radiography preparation state, the mode controller 109 performs switching from the radiography mode RM to the sleep mode SM. Accordingly, it is possible to restrain the drive mode DM from being easily switched to the sleep mode SM in a case where the housing 71 is temporarily stored in the storage portion 27 in the middle of unlocking the movable portions and setting the irradiation portion 23, or the like.

The operation state information SI may be information indicating whether or not at least one of the movable portions of the column portion 21, the arm portion 22, and the swing portion 57 is locked. Furthermore, information indicating whether or not the irradiation portion 23 is in the use state is not limited to the exemplified information indicating whether or not the movable portions are locked. For example, information indicating whether or not a rotation angle of the irradiation portion 23 by the swing portion 57 is a rotation angle of the stored state shown in FIG. 1 may be set as information indicating whether or not the irradiation portion 23 is in the use state. In this case, the second determination unit 121 determines that irradiation portion 23 is not in the use state and the movable radiography apparatus 11 is not in the radiography preparation state in a case where the rotation angle of the irradiation portion 23 by the swing portion 57 is the rotation angle of the stored state. On the contrary, the second determination unit 121 determines that the irradiation portion 23 is in the use state and the movable radiography apparatus 11 is in the radiography preparation state in a case where the rotation angle of the irradiation portion 23 by the swing portion 57 is not the rotation angle of the stored state.

Information indicating whether or not the irradiation portion 23 faces the front surface 76 of the electronic cassette 10 may be set as information indicating whether or not the irradiation portion 23 is in the use state. In regard to the determination about whether or not the irradiation portion 23 faces the front surface 76 of the electronic cassette 10, for example, an electric wave having directivity is emitted from the irradiation portion 23, and in a case where the electric wave is received by the electronic cassette 10, determination is made that the irradiation portion 23 faces the front surface 76 of the electronic cassette 10. In this case, the second determination unit 121 determines that the irradiation portion 23 is not in the use state and the movable radiography apparatus 11 is not in the radiography preparation state in a case where the irradiation portion 23 does not face the front surface 76 of the electronic cassette 10. On the contrary, the second determination unit 121 determines that the irradiation portion 23 is in the use state and the movable radiography apparatus 11 is in the radiography preparation state in a case where the irradiation portion 23 faces the front surface 76 of the electronic cassette 10.

Fourth Embodiment

In a fourth embodiment shown in FIGS. 35 to 38, information indicating whether or not the irradiation field lamp 43 is turned on is set as the operation state information SI.

Figure 35:
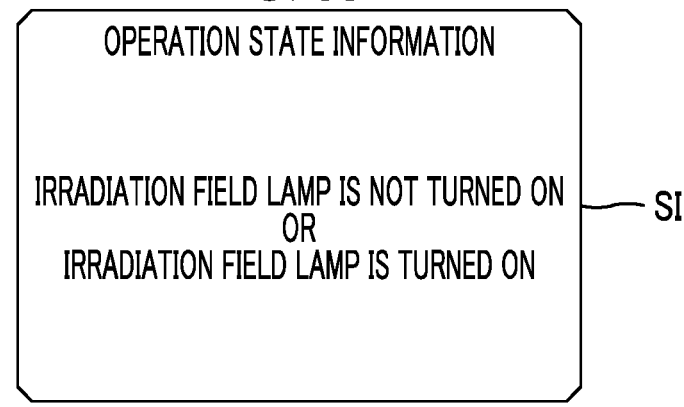
FIG. 35 is a diagram showing operation state information of a fourth embodiment.

As shown in FIG. 35, the operation state information SI of the embodiment has either of a content that the irradiation field lamp 43 is not turned on or a content that the irradiation field lamp 43 is turned on. The acquisition unit 120 acquires, from the movable radiography apparatus 11, the operation state information SI indicating whether or not the irradiation field lamp 43 is turned on and outputs the operation state information SI to the second determination unit 121.

Figure 36:
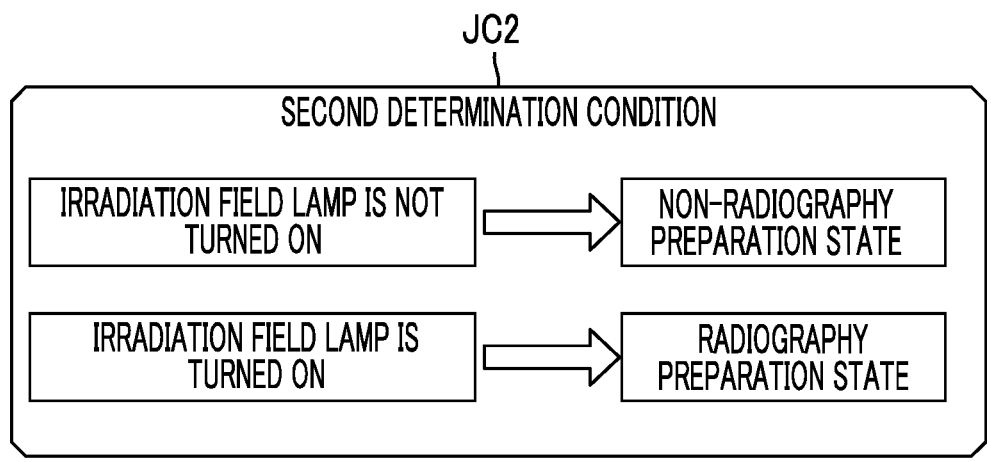
FIG. 36 is a diagram showing a second determination condition of the fourth embodiment.

As shown in FIG. 36, the second determination condition JC2 of the embodiment is a condition for determining that the movable radiography apparatus 11 is not in the radiography preparation state in a case where the irradiation field lamp 43 is not turned on. Furthermore, the second determination condition JC2 is a condition for determining that the movable radiography apparatus 11 is in the radiography preparation state in a case where the irradiation field lamp 43 is turned on. The second determination unit 121 determines whether or not the movable radiography apparatus 11 is in the radiography preparation state according to the second determination condition JC2.

Figure 37:
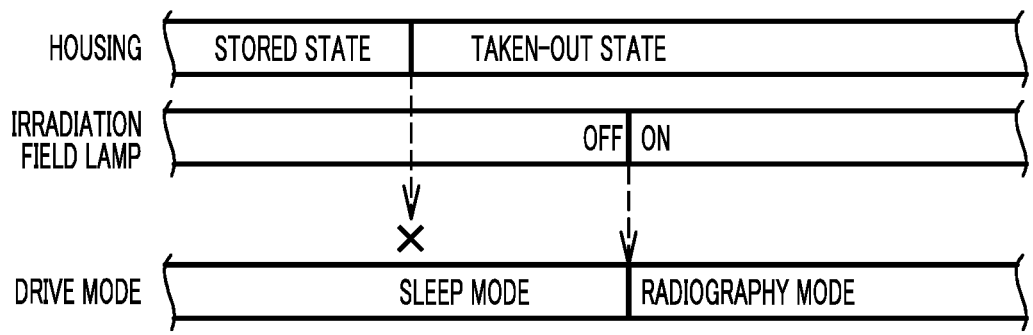
FIG. 37 is a timing chart of mode control of the fourth embodiment.

In a case of the operation state information SI and the second determination condition JC2, as shown in FIG. 37, the mode controller 109 maintains the drive mode DM as the sleep mode SM even while the irradiation field lamp 43 is not turned on after the housing 71 is brought from the stored state into the taken-out state. Then, in a case where the irradiation field lamp 43 is turned on, the mode controller 109 switches the drive mode DM to the radiography mode RM.

Figure 38:
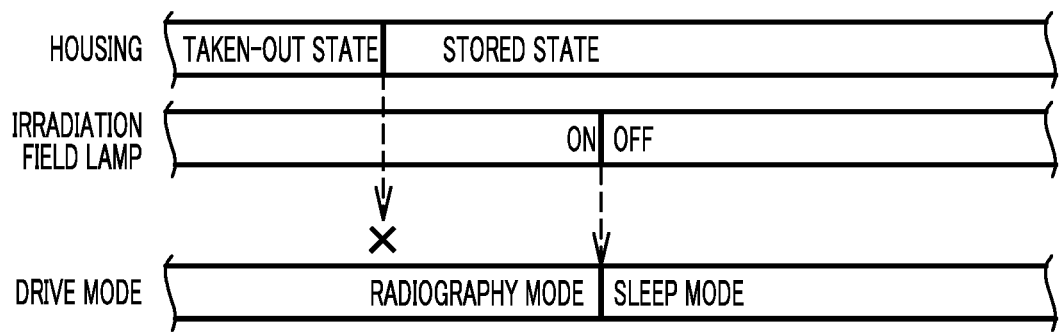
FIG. 38 is a timing chart of mode control of the fourth embodiment.

Furthermore, as shown in FIG. 38, the mode controller 109 maintains the drive mode DM as the radiography mode RM while the irradiation field lamp 43 is turned on even after the housing 71 is brought from the taken-out state into the stored state. Then, in a case where the irradiation field lamp 43 is turned off, the mode controller 109 switches the drive mode DM to the sleep mode SM.

In this way, in the fourth embodiment, the acquisition unit 120 acquires the operation state information SI shown in FIG. 35 indicating whether or not the irradiation field lamp 43 is turned on. According to the second determination condition JC2 shown in FIG. 36, the second determination unit 121 determines that the movable radiography apparatus 11 is not in the radiography preparation state in a case where the irradiation field lamp 43 is not turned on, and determines that the movable radiography apparatus 11 is in the radiography preparation state in a case where the irradiation field lamp 43 is turned on.

As shown in FIG. 37, in a case where the first determination unit 108 determines that the housing 71 is brought from the stored state into the taken-out state, and the operation state information SI has the content that the irradiation field lamp 43 is not turned on, and the second determination unit 121 determines that the movable radiography apparatus 11 is not in the radiography preparation state, the mode controller 109 does not perform switching from the sleep mode SM to the radiography mode RM. In contrast, in a case where the first determination unit 108 determines that the housing 71 is brought from the stored state into the taken-out state, the operation state information SI has the content that the irradiation field lamp 43 is turned on, and the second determination unit 121 determines that the movable radiography apparatus 11 is in the radiography preparation state, the mode controller 109 performs switching from the sleep mode SM to the radiography mode RM. Accordingly, the drive mode DM is restrained from being easily switched to the radiography mode RM although the irradiation field lamp 43 is not turned on and the movable radiography apparatus 11 is not in the radiography preparation state, and it is possible to further suppress wasteful power consumption.

Furthermore, as shown in FIG. 38, in a case where the first determination unit 108 determines that the housing 71 is brought from the taken-out state into the stored state, the operation state information SI has the content that the irradiation field lamp 43 is turned on, and the second determination unit 121 determines that the movable radiography apparatus 11 is in the radiography preparation state, the mode controller 109 does not perform switching from the radiography mode RM to the sleep mode SM. In contrast, in a case where the first determination unit 108 determines that the housing 71 is brought from the taken-out state into the stored state, the operation state information SI has the content that the irradiation field lamp 43 is not turned on, and the second determination unit 121 determines that the movable radiography apparatus 11 is not in the radiography preparation state, the mode controller 109 performs switching from the radiography mode RM to the sleep mode SM. Accordingly, it is possible to restrain the drive mode DM from being easily switched to the sleep mode SM in a case where the housing 71 is temporarily stored in the storage portion 27 in the middle of turning on the irradiation field lamp 43 and confirming the irradiation field, or the like.

Fifth Embodiment

In a fifth embodiment shown in FIGS. 39 to 42, information indicating whether or not communication between the communication unit 91 and the communication unit 26 of the movable radiography apparatus 11 is established is set as the operation state information SI.

Figure 39:
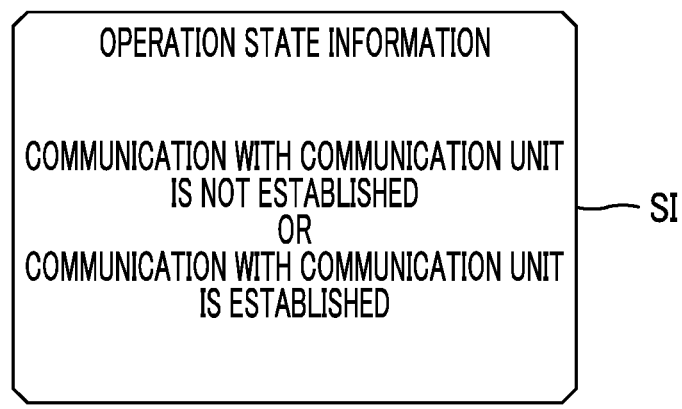
FIG. 39 is a diagram showing operation state information of a fifth embodiment.

As shown in FIG. 39, the operation state information SI of the embodiment has either of a content that communication with the communication unit 26 is not established or a content that communication with the communication unit 26 is established. The acquisition unit 120 acquires, from the communication unit 91, the operation state information SI indicating whether or not communication with the communication unit 26 is established and outputs the operation state information SI to the second determination unit 121. Detection about whether or not communication with the communication unit 26 is established can be performed by the inquiry function of the communication unit 91.

Figure 40:
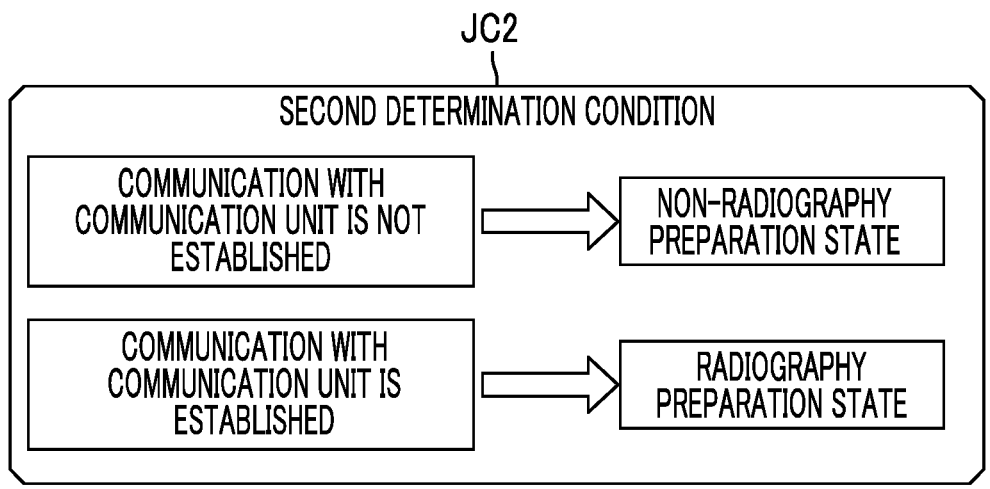
FIG. 40 is a diagram showing a second determination condition of the fifth embodiment.

As shown in FIG. 40, the second determination condition JC2 of the embodiment is a condition for determining that the movable radiography apparatus 11 is not in the radiography preparation state in a case where communication with the communication unit 26 is not established. Furthermore, the second determination condition JC2 is a condition for determining that the movable radiography apparatus 11 is in the radiography preparation state in a case where communication with the communication unit 26 is established. The second determination unit 121 determines whether or not the movable radiography apparatus 11 is in the radiography preparation state according to the second determination condition JC2.

Figure 41:
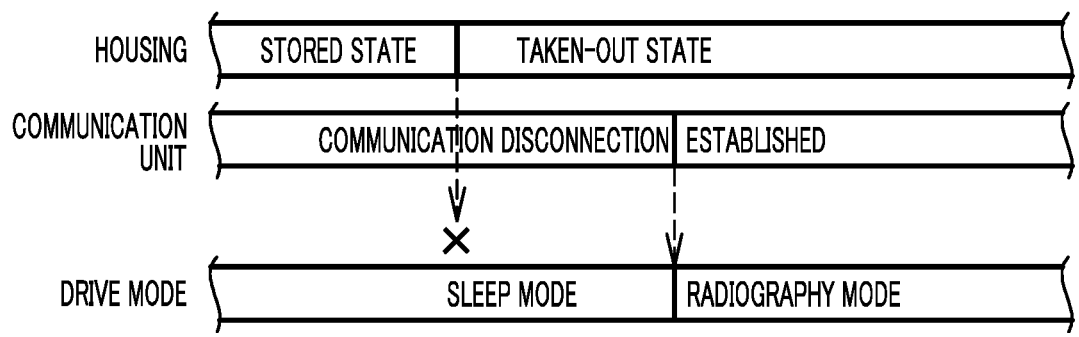
FIG. 41 is a timing chart of mode control of the fifth embodiment.

In a case of the operation state information SI and the second determination condition JC2, as shown in FIG. 41, the mode controller 109 maintains the drive mode DM as the sleep mode SM while communication with the communication unit 26 is not established even after the housing 71 is brought from the stored state into the taken-out state. Then, in a case where communication with the communication unit 26 is established, the mode controller 109 switches the drive mode DM to the radiography mode RM.

Figure 42:
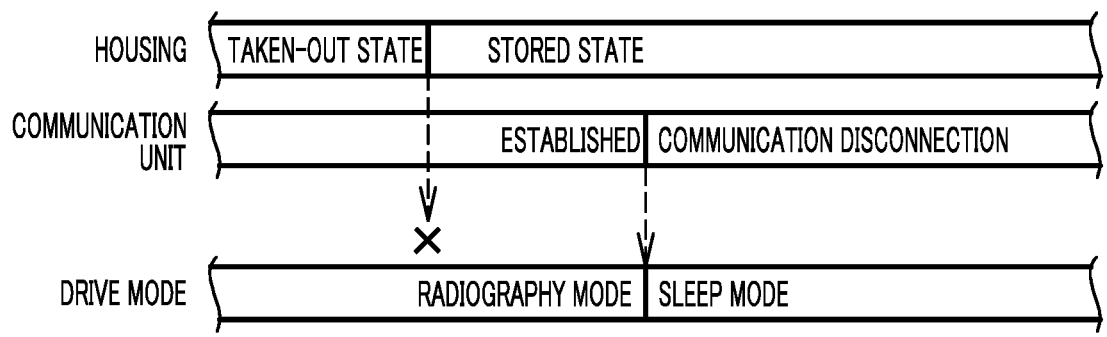
FIG. 42 is a timing chart of mode control of the fifth embodiment.

As shown in FIG. 42, the mode controller 109 maintains the drive mode DM as the radiography mode RM while communication with the communication unit 26 is established even after the housing 71 is brought from the taken-out state into the stored state. Then, in a case where communication with the communication unit 26 is disconnected, the mode controller 109 switches the drive mode DM to the sleep mode SM.

In this way, in the fifth embodiment, the acquisition unit 120 acquires the operation state information SI shown in FIG. 39 indicating whether or not communication with the communication unit 26 is established. According to the second determination condition JC2 shown in FIG. 40, the second determination unit 121 determines that the movable radiography apparatus 11 is not in the radiography preparation state in a case where communication with the communication unit 26 is not established, and the second determination unit 121 determines that the movable radiography apparatus 11 is in the radiography preparation state in a case where communication with the communication unit 26 is established.

As shown in FIG. 41, in a case where the first determination unit 108 determines that the housing 71 is brought from the stored state into the taken-out state, and the operation state information SI has the content that communication with the communication unit 26 is not established, and the second determination unit 121 determines that the movable radiography apparatus 11 is not in the radiography preparation state, the mode controller 109 does not perform switching from the sleep mode SM to the radiography mode RM. In contrast, in a case where the first determination unit 108 determines that the housing 71 is brought from the stored state into the taken-out state, the operation state information SI has the content that communication with the communication unit 26 is established, and the second determination unit 121 determines that the movable radiography apparatus 11 is in the radiography preparation state, the mode controller 109 performs switching from the sleep mode SM to the radiography mode RM. Accordingly, the drive mode DM is restrained from being easily switched to the radiography mode RM although communication with the communication unit 26 is not established and the movable radiography apparatus 11 is not in the radiography preparation state, and it is possible to further suppress wasteful power consumption.

Furthermore, as shown in FIG. 42, in a case where the first determination unit 108 determines that the housing 71 is brought from the taken-out state into the stored state, and the operation state information SI has the content that communication with the communication unit 26 is established, and the second determination unit 121 determines that the movable radiography apparatus 11 is in the radiography preparation state, the mode controller 109 does not perform switching from the radiography mode RM to the sleep mode SM. In contrast, in a case where the first determination unit 108 determines that the housing 71 is brought from the taken-out state into the stored state, the operation state information SI has the content that communication with the communication unit 26 is not established, and the second determination unit 121 determines that the movable radiography apparatus 11 is not in the radiography preparation state, the mode controller 109 performs switching from the radiography mode RM to the sleep mode SM. Accordingly, it is possible to restrain the drive mode DM from being easily switched to the sleep mode SM in a case where the housing 71 is temporarily stored in the storage portion 27 after communication with the communication unit 26 is established, or the like.

The third to fifth embodiments may be implemented in combination. For example, in a case where the third embodiment and the fifth embodiment are implemented in combination, the second determination unit 121 determines that the movable radiography apparatus 11 is not in the radiography preparation state in a case where the irradiation portion 23 is not in the use state and communication with the communication unit 26 is not established. Furthermore, second determination unit 121 determines that the movable radiography apparatus 11 is in the radiography preparation state in a case where irradiation portion 23 is in the use state and communication with the communication unit 26 is established.

Sixth Embodiment

In a sixth embodiment shown in FIGS. 43A to 43H, and 44, the housing 71 can be stored in the storage portion 27 in a plurality of directions.

In the above-described first embodiment, as shown in FIG. 7, although the storage direction of the housing 71 in the storage portion 27 is one direction, in the embodiment, as shown in FIGS. 43A to 43H, the housing 71 is stored in the storage portion 27 in a plurality of directions. Specifically, the housing 71 is stored in the storage portion 27 in eight directions in total of a pattern 1 shown in FIG. 43A, a pattern 2 shown in FIG. 43B, a pattern 3 shown in FIG. 43C, a pattern 4 shown in FIG. 43D, a pattern 5 shown in FIG. 43E, a pattern 6 shown in FIG. 43F, a pattern 7 shown in FIG. 43G, and a pattern 8 shown in FIG. 43H.

The pattern 1 of FIG. 43A is a pattern in which the front surface 76 turns toward the handle 28, and the housing 71 is stored in the storage portion 27 from the lower surface 79 like the case shown in FIG. 7. The pattern 2 of FIG. 43B is a pattern obtained by reversing the top and bottom of the pattern 1, and the pattern 3 of FIG. 43C is a pattern obtained by reversing the front and rear of the pattern 1. The pattern 4 of FIG. 43D is a pattern obtained by reversing the top and bottom and the front and rear of the pattern 1.

The pattern 5 of FIG. 43E is a pattern obtained by rotating the housing 71 clockwise at 90° from the pattern 1. The pattern 6 of FIG. 43F is a pattern obtained by rotating the housing 71 counterclockwise at 90° from the pattern 1, and the pattern 7 of FIG. 43G is a pattern obtained by reversing the front and rear of the pattern 1 and rotating the housing 71 counterclockwise at 90° from the pattern 1. The pattern 8 of FIG. 43H is a pattern obtained by reversing the front and rear of the pattern 1 and rotating the housing 71 clockwise at 90° from the pattern 1. In this case, the standard poses SP are eight standard poses of a standard pose SP_1 of FIG. 43A, a standard pose SP_2 of FIG. 43B, . . . , a standard pose SP_7 of FIG. 43G, and a standard pose SP_8 of FIG. 43H corresponding to eight directions.

Figure 44:
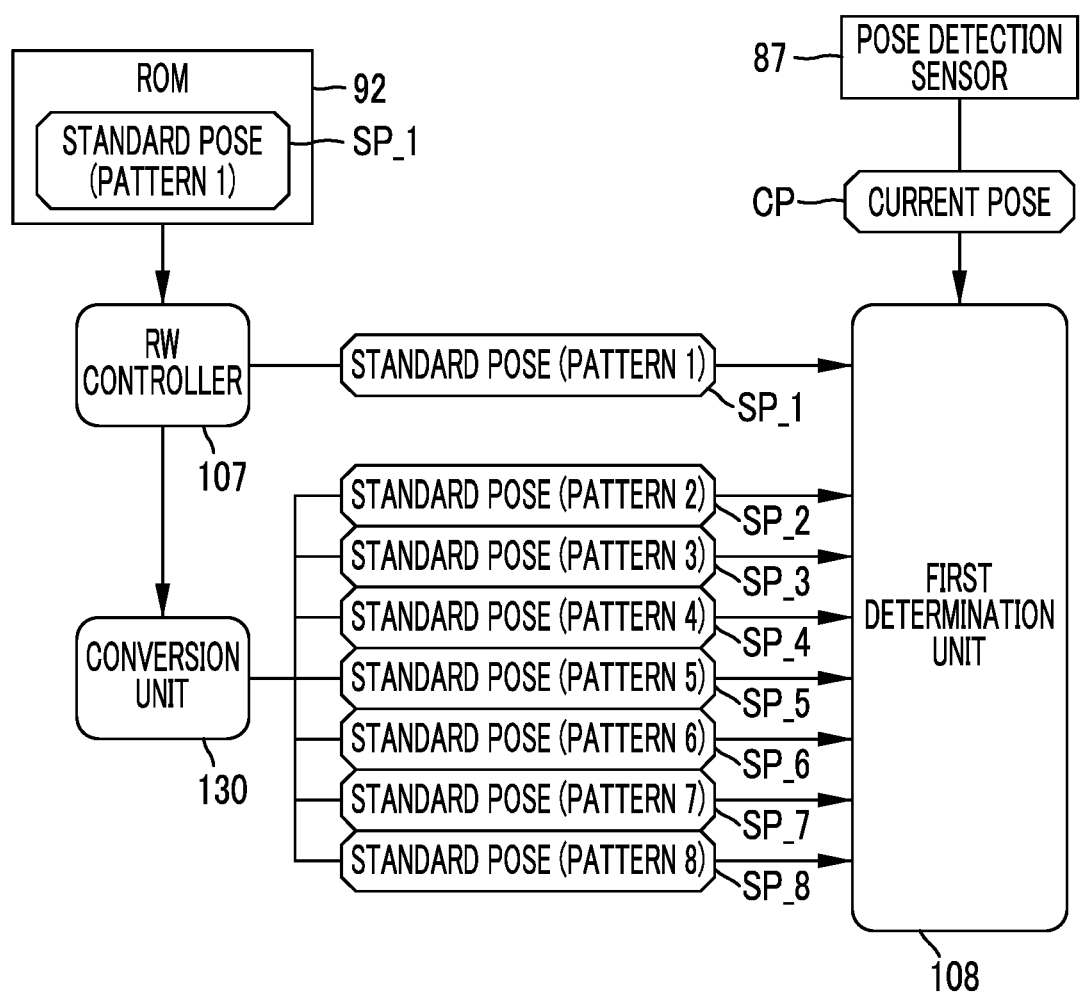
FIG. 44 is a diagram showing a manner in which the first determination unit performs determination based on a plurality of standard poses and a current pose.

As shown in FIG. 44, for example, only the standard pose SP_1 of the pattern 1 of FIG. 43A is stored in the ROM 92. The RW controller 107 reads the standard pose SP_1 from the ROM 92 and outputs the standard pose SP_1 to the first determination unit 108 and the conversion unit 130. The conversion unit 130 converts the standard poses SP_2 to SP_8 of the remaining patterns 2 to 8 from the standard pose SP_1. The conversion unit 130 outputs the converted standard poses SP_2 to SP_8 to the first determination unit 108. The first determination unit 108 performs determination based on the eight standard poses SP_1 to SP_8 and the current pose CP from the pose detection sensor 87. As described above, since the patterns 2 to 8 have a geometrical relationship of top-bottom inversion, front-rear inversion, and rotation at 90° with the pattern 1, the conversion in the conversion unit 130 is performed by simple geometrical calculation.

In this way, in the sixth embodiment, as shown in FIGS. 43A to 43H, the housing 71 is stored in the storage portion 27 in a plurality of directions, and there are a plurality of standard poses SP (the standard poses SP_1 to SP_8) corresponding to a plurality of directions. Then, as shown in FIG. 44, the first determination unit 108 performs determination based on a plurality of standard poses SP_1 to SP_8 and the current pose CP. Accordingly, it is possible to cope with even a case where there are a plurality of storage directions of the housing 71 in the storage portion 27.

In FIGS. 43A to 43H, although a maximum of eight storage directions to be considered is shown, the technique of the present disclosure is not limited thereto. For example, the number of storage directions may be four of the pattern 1 to the pattern 4 shown in FIG. 43A to 43D, or the number of storage directions may be two of the patterns 7 and 8 shown in FIGS. 43G and 43H. The standard pose SP that is stored in the ROM 92 may be at least one of a plurality of standard poses SP corresponding to a plurality of directions. All of a plurality of standard poses SP corresponding to a plurality of directions may be stored in the ROM 92. In this case, the conversion unit 130 is not needed.

Seventh Embodiment

Figure 45:
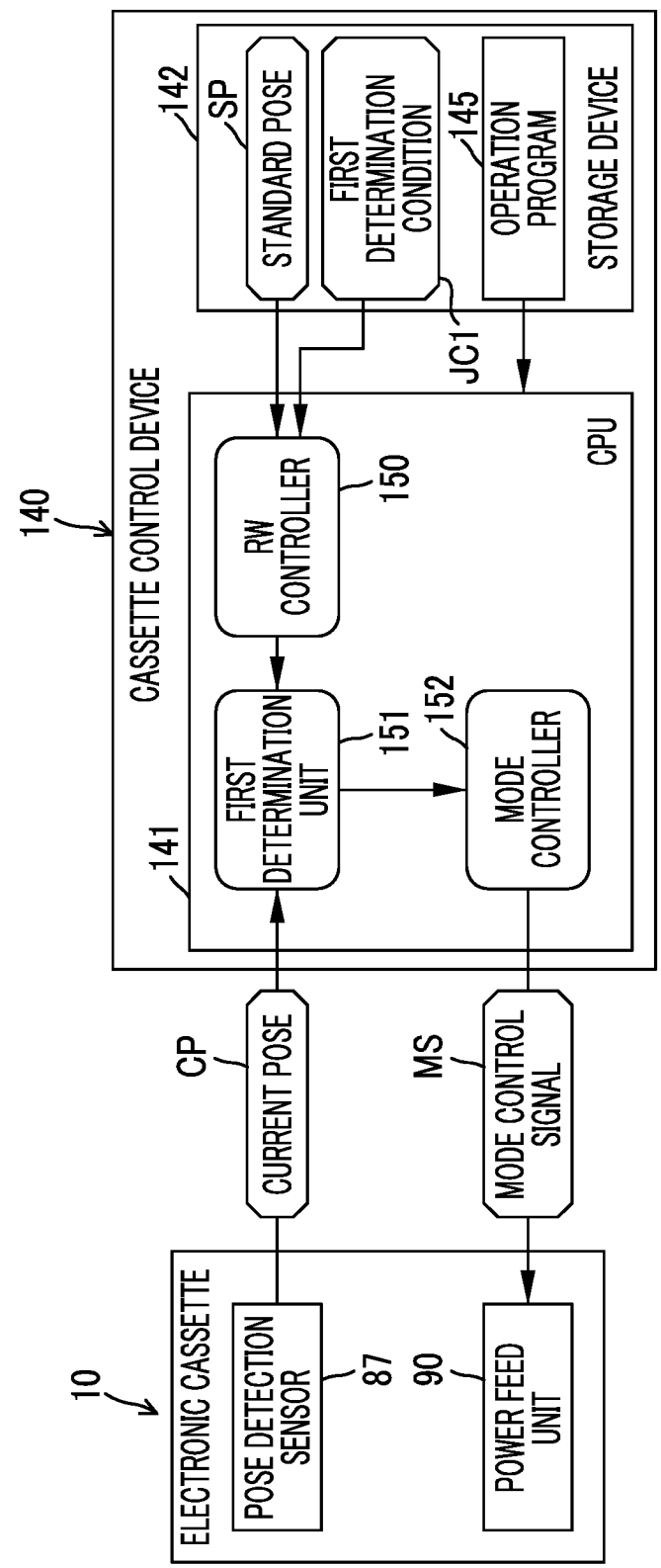
FIG. 45 is a diagram showing a cassette control device.

In a seventh embodiment shown in FIG. 45, the functions of the electronic cassette 10 of the respective embodiments are charged on a cassette control device 140.

As shown in FIG. 45, the cassette control device 140 comprises a CPU 141 and a storage device 142. The storage device 142 is, for example, a hard disk drive. In the storage device 142, an operation program 145 is stored. The operation program 145 is the substantially same program as the operation program 100 shown in FIG. 9, except that the functions of the image output controller 105 and the communication controller 106 are not implemented.

In the storage device 142, the standard pose SP and the first determination condition JC1 are stored like the ROM 92 of the above-described first embodiment. That is, the storage device 142 is an example of a "storage unit" related to the technique of the present disclosure.

The CPU 141 executes the operation program 145, thereby functioning as a RW controller 150, a first determination unit 151, and a mode controller 152 in cooperation with the RAM (not shown) and the like. The RW controller 150 has the same functions as the RW controller 107, and is an example of a "first acquisition unit" related to the technique of the present disclosure. Furthermore, the first determination unit 151 has the same functions as the first determination unit 108, and the mode controller 152 has the same functions as the mode controller 109. Note that the current pose CP from the pose detection sensor 87 of the electronic cassette 10 is input to the first determination unit 151. Furthermore, the mode controller 152 transmits the mode control signal MS toward the power feed unit 90 of the electronic cassette 10.

In this way, in the seventh embodiment, the cassette control device 140 has the functions of the RW controller 150, the first determination unit 151, and the mode controller 152. Accordingly, it is possible to reduce a processing load of the electronic cassette 10.

Various modifications can be made to the hardware configuration of a computer constituting the cassette control device 140. For example, the cassette control device 140 may be constituted of a plurality of computers separated as hardware for the purpose of improving processing capability or reliability. Specifically, the functions of the RW controller 150 and the functions of the first determination unit 151 and the mode controller 152 may be distributed and charged on two computers. In this case, the cassette control device 140 is constituted of two computers.

In this case, the hardware configuration of the computer can be appropriately changed according to requested performance, such as processing capability, safety, and reliability. In addition, the technique of the present disclosure is not limited to hardware, and the application program, such as the operation programs 100 and 145, may be duplexed or may be of course distributed and stored in a plurality of storage devices for the purpose of securing safety or reliability.

In the embodiments described above, as the hardware structures of the processing units that execute various kinds of processing, for example, the image output controller 105, the communication controller 106, the RW controllers 107 and 150, the first determination units 108 and 151, the mode controllers 109 and 152, the acquisition units 120, the second determination unit 121, and the conversion unit 130, various processors described below can be used. Various processors include a programmable logic device (PLD) that is a processor capable of changing a circuit configuration after manufacture, such as a field programmable gate array (FPGA), a dedicated electric circuit that is a processor having a circuit configuration dedicatedly designed for executing specific processing, such as an application specific integrated circuit (ASIC), and the like, in addition to a central processing unit (CPU) that is a general-purpose processor executing software (program) to function as various processing units, as described above.

One processing unit may be configured of one of various processors described above or may be configured of a combination of two or more processors (for example, a plurality of FPGAs or a combination of a CPU and an FPGA) of the same type or different types. A plurality of processing units may be configured of one processor.

As an example where a plurality of processing units are configured of one processor, first, as represented by a computer, such as a client or a server, there is a form in which one processor is configured of a combination of one or more CPUs and software, and the processor functions as a plurality of processing units. Secondly, as represented by system on chip (SoC) or the like, there is a form in which a processor that implements all functions of a system including a plurality of processing units into one integrated circuit (IC) chip is used. In this way, various processing units may be configured using one or more processors among various processors described above as a hardware structure.

In addition, the hardware structure of various processors is, more specifically, an electric circuit (circuitry) in which circuit elements, such as semiconductor elements, are combined.

From the above description, it is possible to ascertain the invention described in the following supplementary items 1 and 2.

Supplementary Item 1

An electronic cassette comprising:

an image output unit that detects radiation transmitted through a subject and outputs a radiographic image represented by an electrical signal;

a portable housing in which the image output unit is incorporated;

a first acquisition processor that acquires a standard pose as a pose of the housing in a stored state, in which the housing is stored in a storage portion of a movable radiography apparatus, from a storage unit;

a first determination processor that determines whether the housing is in the stored state or a taken-out state, in which the housing is taken out from the storage portion, based on the standard pose and a current pose as a current pose of the housing detected by a pose detection sensor; and a mode control processor that controls a drive mode including a radiography mode where the radiographic image is able to be output from the image output unit and a sleep mode where power consumption is smaller than in the radiography mode, and switches the drive mode from the sleep mode to the radiography mode in a case where the first determination processor determines that the housing is brought from the stored state into the taken-out state.

Supplementary Item 2

A cassette control device that controls an electronic cassette comprising an image output unit that detects radiation transmitted through a subject and outputs a radiographic image represented by an electrical signal, a portable housing in which the image output unit is incorporated, the cassette control device comprising:

a first acquisition processor that acquires a standard pose as a pose of the housing in a stored state, in which the housing is stored in a storage portion of a movable radiography apparatus, from a storage unit;

a first determination processor that determines whether the housing is in the stored state or a taken-out state, in which the housing is taken out from the storage portion, based on the standard pose and a current pose as a current pose of the housing detected by a pose detection sensor; and a mode control processor that controls a drive mode including a radiography mode where the radiographic image is able to be output from the image output unit and a sleep mode where power consumption is smaller than in the radiography mode, and switches the drive mode from the sleep mode to the radiography mode in a case where the first determination processor determines that the housing is brought from the stored state into the taken-out state.

In the technique of the present disclosure, it is possible to appropriately combine various embodiments described above and various modification examples. The technique of the present disclosure is not limited to the above-described embodiments, and various configurations can be of course employed without departing from the spirit and scope of the technique of the present disclosure. In addition to the program, the technique of the present disclosure extends to a storage medium that stores the program in a non-transitory manner.

The foregoing description and drawings are detailed description on portions related to the technique of the present disclosure, and is just an example of the technique of the present disclosure. For example, the description of the configurations, the functions, the operations, and the effects described above is the description relating to an example of the configurations, the functions, the operations, and the effects of the portions related to the technique of the present disclosure. Thus, it is needless to say that an unnecessary portion may be deleted or a new element may be added or replaced with respect to the foregoing description and drawings without departing from the spirit and scope of the technique of the present disclosure. In order to avoid complication and facilitate understanding a portion related to the technique of the present disclosure, in the foregoing description and drawings, description relating to common general technical knowledge or the like not requiring particular description while enabling to carry out the technique of the present disclosure is omitted.

All of the documents, patent applications, and technical standards in the specification are incorporated herein by reference to the same extent that the individual documents, patent applications, and technical standards are described specifically and independently.

What is claimed is:

1. An electronic cassette comprising:
   a radiation detection sensor that detects radiation transmitted through a subject and outputs a radiographic image represented by an electrical signal;
   a portable housing in which the radiation detection sensor is incorporated;
   a pose detection sensor that detects a current pose as a current pose of the housing;
   a processor that is configured to:
      acquire a standard pose as a pose of the housing in a stored state, in which the housing is stored in a cassette accommodating box of a movable radiography apparatus having wheels, from a memory; and
      determine whether the housing is in the stored state or a taken-out state, in which the housing is taken out from the cassette accommodating box, based on the standard pose and the current pose; and
   a mode controller that controls a drive mode including a radiography mode where the radiographic image is able to be output from the radiation detection sensor and a sleep mode where power consumption is smaller than in the radiography mode, and switches the drive mode from the sleep mode to the radiography mode in a case where the processor determines that the housing is brought from the stored state into the taken-out state.

2. The electronic cassette according to claim 1, wherein the processor determines that the housing is brought from the stored state into the taken-out state in a case where a state in which the current pose is deviated from the standard pose by a preset threshold value or more is continued for a preset period.

3. The electronic cassette according to claim 1, wherein the mode controller switches the drive mode from the radiography mode to the sleep mode in a case where the processor determines that the housing is brought from the taken-out state into the stored state.

4. The electronic cassette according to claim 3, wherein:
   the processor acquires operation state information indicating an operation state of the movable radiography apparatus, the processor determines whether or not the movable radiography apparatus is in a radiography preparation state based on the operation state information, wherein the mode controller does not perform switching from the sleep mode to the radiography mode in a case where the processor determines that the housing is brought from the stored state into the taken-out state, and the processor determines that the movable radiography apparatus is not in the radiography preparation state, and performs switching from the sleep mode to the radiography mode in a case where the processor determines that the housing is brought from the stored state into the taken-out state, and the processor determines that the movable radiography apparatus is in the radiography preparation state.

5. The electronic cassette according to claim 4, wherein the movable radiography apparatus comprises an irradiation emitter having a radiation tube that emits the radiation and being able to change a position with respect to the subject, and the operation state information is information indicating whether or not the irradiation emitter is in a use state.

6. The electronic cassette according to claim 5, wherein the mode controller does not perform switching from the sleep mode to the radiography mode in a case where the processor determines that the housing is brought from the stored state into the taken-out state, and the operation state information has a content that the irradiation emitter is not in the use state and the processor determines that the movable radiography apparatus is not in the radiography preparation state, and performs switching from the sleep mode to the radiography mode in a case where the processor determines that the housing is brought from the stored state into the taken-out state, the operation state information has a content that the irradiation emitter is in the use state, and the processor determines that the movable radiography apparatus is in the radiography preparation state.

7. The electronic cassette according to claim 5, wherein the operation state information is information indicating whether or not a movable portion changing the position of the irradiation emitter with respect to the subject is locked, and the processor determines that the irradiation emitter is not in the use state and the movable radiography apparatus is not in the radiography preparation state in a case where the movable portion is locked, and determines that the irradiation emitter is in the use state and the movable radiography apparatus is in the radiography preparation state in a case where the movable portion is not locked.

8. The electronic cassette according to claim 4, wherein the movable radiography apparatus comprises an irradiation field lamp that emits light representing an irradiation field of the radiation, and the operation state information is information indicating whether or not the irradiation field lamp is turned on.

9. The electronic cassette according to claim 8, wherein the mode controller does not perform switching from the sleep mode to the radiography mode in a case where the processor determines that the housing is brought from the stored state into the taken-out state, and the operation state information has a content that the irradiation field lamp is not turned on, and the processor determines that the movable radiography apparatus is not in the radiography preparation state, and performs switching from the sleep mode to the radiography mode in a case where the processor determines that the housing is brought from the stored state into the taken-out state, the operation state information has a content that the irradiation field lamp is turned on, and the processor determines that the movable radiography apparatus is in the radiography preparation state.

10. The electronic cassette according to claim 4, wherein the movable radiography apparatus comprises a wireless communication device using antennas or a connector, and the operation state information is information indicating whether or not communication with the wireless communication device is established.

11. The electronic cassette according to claim 10, wherein the mode controller does not perform switching from the sleep mode to the radiography mode in a case where the processor determines that the housing is brought from the stored state into the taken-out state, and the operation state information has a content that communication is not established, and the processor determines that the movable radiography apparatus is not in the radiography preparation state, and performs switching from the sleep mode to the radiography mode in a case where the processor determines that the housing is brought from the stored state into the taken-out state, the operation state information has a content that communication is established, and the processor determines that the movable radiography apparatus is in the radiography preparation state.

12. The electronic cassette according to claim 4, wherein the mode controller does not perform switching from the radiography mode to the sleep mode in a case where the first determination unit determines that the housing is brought from the taken-out state into the stored state, and the processor determines that the movable radiography apparatus is in the radiography preparation state, and performs switching from the radiography mode to the sleep mode in a case where the processor determines that the housing is brought from the taken-out state into the stored state, and the processor determines that the movable radiography apparatus is not in the radiography preparation state.

13. The electronic cassette according to claim 1, wherein the memory that stores the standard pose is incorporated.

14. The electronic cassette according to claim 1, wherein the housing is stored in the cassette accommodating box in a plurality of directions, a plurality of the standard poses are provided corresponding to the plurality of directions, and the processor performs the determination based on the plurality of standard poses and the current pose.

15. A method of operating an electronic cassette comprising a radiation detection sensor that detects radiation transmitted through a subject and outputs a radiographic image represented by an electrical signal and a portable housing in which the radiation detection sensor is incorporated, the method comprising:

a first acquisition step of acquiring a standard pose as a pose of the housing in a stored state, in which the housing is stored in a cassette accommodating box of a movable radiography apparatus having wheels, from a memory;
a first determination step of determining whether the housing is in the stored state or a taken-out state, in which the housing is taken out from the cassette accommodating box, based on the standard pose and a current pose as a current pose of the housing detected by a pose detection sensor; and
a mode control step of controlling a drive mode including a radiography mode where the radiographic image is able to be output from the radiation detection sensor and a sleep mode where power consumption is smaller than in the radiography mode, and switching the drive mode from the sleep mode to the radiography mode in a case where determination is made in the first determination step that the housing is brought from the stored state into the taken-out state.

16. A non-transitory computer-readable storage medium storing an operation program for an electronic cassette comprising a radiation detection sensor that detects radiation transmitted through a subject and outputs a radiographic image represented by an electrical signal and a portable housing in which the radiation detection sensor is incorporated, the operation program causing a computer to function as:
a first acquisition unit that acquires a standard pose as a pose of the housing in a stored state, in which the housing is stored in a cassette accommodating box of a movable radiography apparatus having wheels, from a memory;
a first determination unit that determines whether the housing is in the stored state or a taken-out state, in which the housing is taken out from the cassette accommodating box, based on the standard pose and a current pose as a current pose of the housing detected by a pose detection sensor; and
a mode controller that controls a drive mode including a radiography mode where the radiographic image is able to be output from the radiation detection sensor and a sleep mode where power consumption is smaller than in the radiography mode, and switches the drive mode from the sleep mode to the radiography mode in a case where the first determination unit determines that the housing is brought from the stored state into the taken-out state.

17. A cassette control device that controls an electronic cassette comprising a radiation detection sensor that detects radiation transmitted through a subject and outputs a radiographic image represented by an electrical signal and a portable housing in which the radiation detection sensor is incorporated, the cassette control device comprising:
a processor that is configured to:
acquire a standard pose as a pose of the housing in a stored state, in which the housing is stored in a cassette accommodating box of a movable radiography apparatus having wheels, from a memory; and
determine whether the housing is in the stored state or a taken-out state, in which the housing is taken out from the cassette accommodating box, based on the standard pose and a current pose as a current pose of the housing detected by a pose detection sensor; and
a mode controller that controls a drive mode of the electronic cassette including a radiography mode where the radiographic image is able to be output from the radiation detection sensor and a sleep mode where power consumption is smaller than in the radiography mode, and switches the drive mode from the sleep mode to the radiography mode in a case where the processor determines that the housing is brought from the stored state into the taken-out state.

18. A radiography system comprising:
an electronic cassette having a radiation detection sensor that detects radiation transmitted through a subject and outputs a radiographic image represented by an electrical signal and a portable housing in which the radiation detection sensor is incorporated;
a movable radiography apparatus having a cassette accommodating box and wheels, in which the electronic cassette is stored;
a processor that is configured to:
acquire a standard pose as a pose of the housing in a stored state, in which the housing is stored in the cassette accommodating box, from a memory;
determine whether the housing is in the stored state or a taken-out state, in which the housing is taken out from the cassette accommodating box, based on the standard pose and a current pose as a current pose of the housing detected by a pose detection sensor; and
a mode controller that controls a drive mode of the electronic cassette including a radiography mode where the radiographic image is able to be output from the radiation detection sensor and a sleep mode where power consumption is smaller than in the radiography mode, and switches the drive mode from the sleep mode to the radiography mode in a case where the processor determines that the housing is brought from the stored state into the taken-out state.

19. A method of operating a radiography system comprising an electronic cassette having a radiation detection sensor that detects radiation transmitted through a subject and outputs a radiographic image represented by an electrical signal and a portable housing in which the radiation detection sensor is incorporated, and a movable radiography apparatus having a cassette accommodating box and wheels, in which the electronic cassette is stored, the method comprising:
a first acquisition step of acquiring a standard pose as a pose of the housing in a stored state, in which the housing is stored in the cassette accommodating box, from a memory;
a first determination step of determining whether the housing is in the stored state or a taken-out state, in which the housing is taken out from the cassette accommodating box, based on the standard pose and a current pose as a current pose of the housing detected by a pose detection sensor; and
a mode control step of controlling a drive mode of the electronic cassette including a radiography mode where the radiographic image is able to be output from the radiation detection sensor and a sleep mode where power consumption is smaller than in the radiography mode, and switching the drive mode from the sleep mode to the radiography mode in a case where determination is made in the first determination step that the housing is brought from the stored state into the taken-out state.

* * * * *